(12) United States Patent
Hikosaka et al.

(10) Patent No.: US 12,267,568 B2
(45) Date of Patent: Apr. 1, 2025

(54) RADIATION IMAGING CONTROL APPARATUS, IMAGE PROCESSING APPARATUS, RADIATION IMAGING CONTROL METHOD, IMAGE PROCESSING METHOD, STORAGE MEDIUM, AND RADIATION IMAGING SYSTEM

(71) Applicant: CANON KABUSHIKI KAISHA, Tokyo (JP)

(72) Inventors: Manami Hikosaka, Kanagawa (JP); Yuichi Ikeda, Shizuoka (JP); Yasutomo Shimizu, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 253 days.

(21) Appl. No.: 17/841,101

(22) Filed: Jun. 15, 2022

(65) Prior Publication Data

US 2022/0311956 A1    Sep. 29, 2022

Related U.S. Application Data

(63) Continuation of application No. PCT/JP2020/045642, filed on Dec. 8, 2020.

(30) Foreign Application Priority Data

Dec. 19, 2019 (JP) ................. 2019-229706
Dec. 19, 2019 (JP) ................. 2019-229707

(51) Int. Cl.
*H04N 23/11* (2023.01)
*H04N 23/63* (2023.01)

(52) U.S. Cl.
CPC ........... *H04N 23/11* (2023.01); *H04N 23/632* (2023.01)

(58) Field of Classification Search
CPC ...... H04N 23/11; H04N 23/632; H04N 23/61; A61B 6/54; A61B 6/00; G01V 5/20; G06V 10/25; G06V 10/273; G06V 2201/03
See application file for complete search history.

(56) References Cited

U.S. PATENT DOCUMENTS

| | | |
|---|---|---|
| 2013/0136323 A1 | 5/2013 | Asiyanbola et al. |
| 2015/0265228 A1 | 9/2015 | Kyriakou |
| | (Continued) | |

FOREIGN PATENT DOCUMENTS

| | | |
|---|---|---|
| JP | H02-42436 A | 2/1990 |
| JP | 2001307069 A | 11/2001 |
| | (Continued) | |

*Primary Examiner* — Michael E Teitelbaum
(74) *Attorney, Agent, or Firm* — Canon U.S.A., Inc. IP Division

(57) ABSTRACT

A radiation imaging control apparatus according to an aspect of the present invention includes an image acquisition unit configured to acquire a captured image obtained by capturing an image of a subject, a foreign matter detection unit configured to detect, in a case where a radiation image of the subject is to be acquired, a foreign matter which is likely to appear in the radiation image from the captured image acquired by the image acquisition unit, a warning information generation unit configured to generate warning information regarding image capturing of a radiation image based on the foreign matter detection unit having detected a foreign matter in the captured image, and a display control unit configured to issue a notification based on the warning information.

14 Claims, 17 Drawing Sheets

(56) References Cited

U.S. PATENT DOCUMENTS

| | | | |
|---|---|---|---|
| 2018/0188191 A1 | 7/2018 | Davis, III | |
| 2019/0021677 A1 | 1/2019 | Grbic et al. | |
| 2019/0069871 A1* | 3/2019 | Tkaczyk | A61B 6/4452 |

FOREIGN PATENT DOCUMENTS

| | | | |
|---|---|---|---|
| JP | 2005210467 A | 8/2005 |
| JP | 2011024721 A | 2/2011 |
| JP | 2013158431 A | 8/2013 |
| JP | 201735294 A | 2/2017 |

* cited by examiner

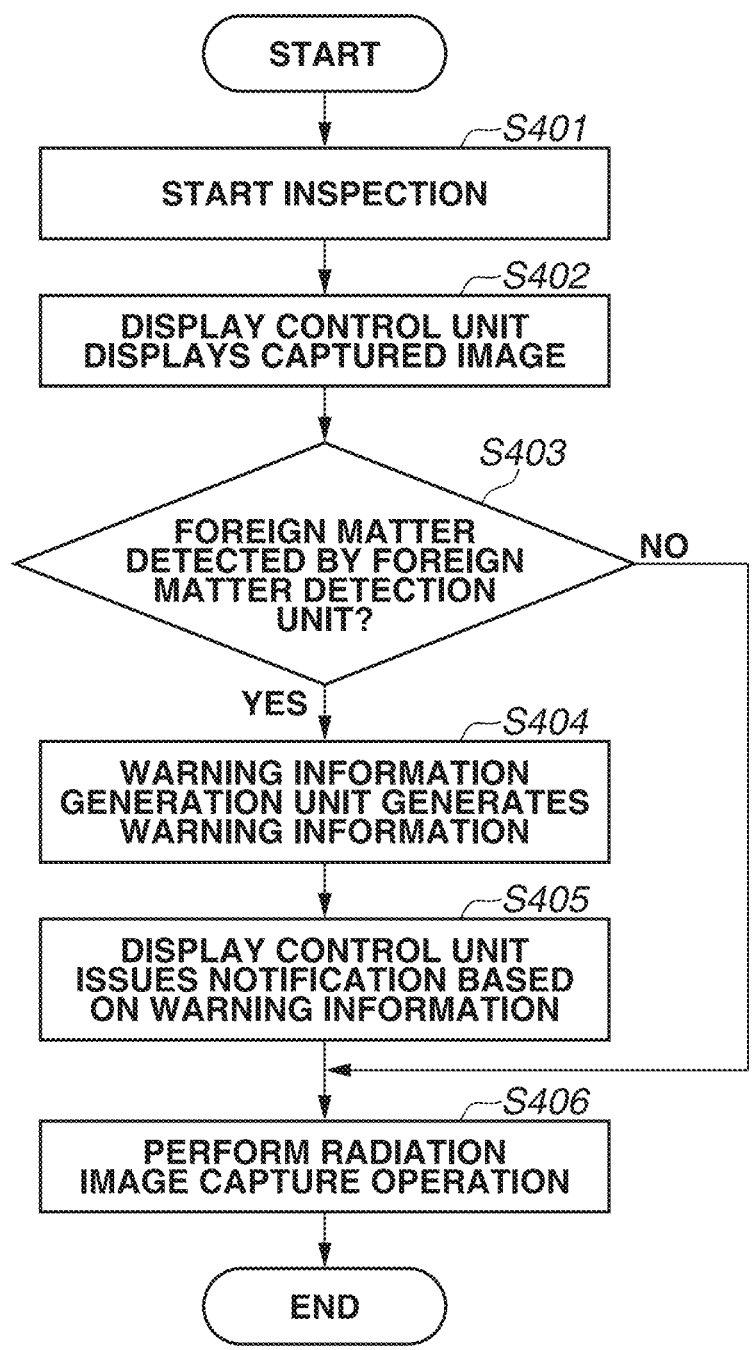

FIG.15

| ABNORMALITIES TO BE REPORTED: | ENABLED | CATEGORY OF ABNORMALITY |
|---|---|---|
| | · | BLEEDING |
| | ☐ | BRUISE |
| | · | FRACTURE |
| | ☐ | RASH |

1700
1710
1720
1730 — OK

RADIATION IMAGING CONTROL APPARATUS, IMAGE PROCESSING APPARATUS, RADIATION IMAGING CONTROL METHOD, IMAGE PROCESSING METHOD, STORAGE MEDIUM, AND RADIATION IMAGING SYSTEM

CROSS-REFERENCE TO RELATED APPLICATIONS

This application is a Continuation of International Patent Application No. PCT/JP2020/045642, filed Dec. 8, 2020, which claims the benefit of Japanese Patent Applications No. 2019-229706, filed Dec. 19, 2019, and No. 2019-229707, filed Dec. 19, 2019, all of which are hereby incorporated by reference herein in their entirety.

BACKGROUND OF THE INVENTION

Field of the Invention

The present invention relates to a radiation imaging control apparatus, an image processing apparatus, a radiation imaging control method, an image processing method, a storage medium, and a radiation imaging system.

Background Art

Radiation imaging systems using radiation are known as imaging systems in the medical field. In a radiation imaging system, a radiation imaging apparatus is irradiated with a radiation emitted by a radiation generation apparatus through a target patient, and the radiation imaging apparatus generates a radiation image. Thus, it is possible for the user to check the radiation image immediately after radiation image capturing.

PTL 1 discusses a radiation diagnosis apparatus which prevents undesired re-imaging by radiation image capturing. An image captured by an optical camera attached to the radiation generation apparatus is displayed on the screen of the radiation diagnosis apparatus. The radiation diagnosis apparatus then compares an image for positioning when the user positions the orientation of a target patient with the image captured by the optical camera. If the orientation of the target patient is mismatched between the images, the user is notified of the mismatching, thus preventing undesired radiation re-imaging due to the body movement of the target patient.

CITATION LIST

Patent Literature

PTL 1: Japanese Patent Laid-Open No. 2011-24721

However, depending on foreign matters which appear in a radiation image, such as buttons of clothes and a necklace, radiation re-imaging may become necessary. In recent years, there are cases where a user cannot sufficiently pay attention to foreign matters which will appear in a radiation image. Examples of such cases include a case where a radiation image is captured with a target patient wearing clothes from the viewpoint of privacy of the target patient and a case where a radiation image is captured for a number of target patients as in a group medical examination. PTL 1 does not discuss a configuration for preventing undesired radiation re-imaging due to foreign matters appearing in a radiation image.

The present invention has been embodied in view of the above-described issue and is directed to providing a radiation imaging control apparatus that prevents the undesired radiation re-imaging by detecting a foreign matter which is likely to appear in a radiation image and displaying a warning before radiation image capturing.

SUMMARY OF THE INVENTION

According to an aspect of the present invention, a radiation imaging control apparatus includes an image acquisition unit configured to acquire a captured image obtained by capturing an image of a subject, a foreign matter detection unit configured to detect, in a case where a radiation image of the subject is to be acquired, a foreign matter which is likely to appear in the radiation image from the captured image acquired by the image acquisition unit, a warning information generation unit configured to generate warning information regarding image capturing of a radiation image based on the foreign matter detection unit having detected a foreign matter in the captured image, and a display control unit configured to issue a notification based on the warning information.

Further features of the present invention will become apparent from the following description of exemplary embodiments with reference to the attached drawings.

BRIEF DESCRIPTION OF THE DRAWINGS

FIG. 4 is a flowchart illustrating processing of the radiation imaging control apparatus according to the first exemplary embodiment.

FIG. 15 illustrates an example of a setting screen according to a fifth exemplary embodiment.

DESCRIPTION OF THE EMBODIMENTS

Exemplary embodiments of the present invention will be described below with reference to the accompanying drawings. The present invention is not limited to the exemplary embodiments disclosed below but can be modified and changed in diverse manners without departing from the ambit of the appended claims.

Foreign matters which are likely to appear in a radiation image to be used below refer to objects which is likely to appear in a radiation image acquired in radiation image capturing. Examples of objects which is likely to appear in a radiation image include plastics, such as glasses and buttons, metals, such as belts and fasteners, printing of T-shirts, transdermal therapeutic patches, and heat pads. Foreign matters which are likely to appear in a radiation image are not limited thereto.

First Exemplary Embodiment

A configuration of a radiation imaging system according to a first present exemplary embodiment will be described below with reference to FIGS. 1 to 3.

Figure 1:
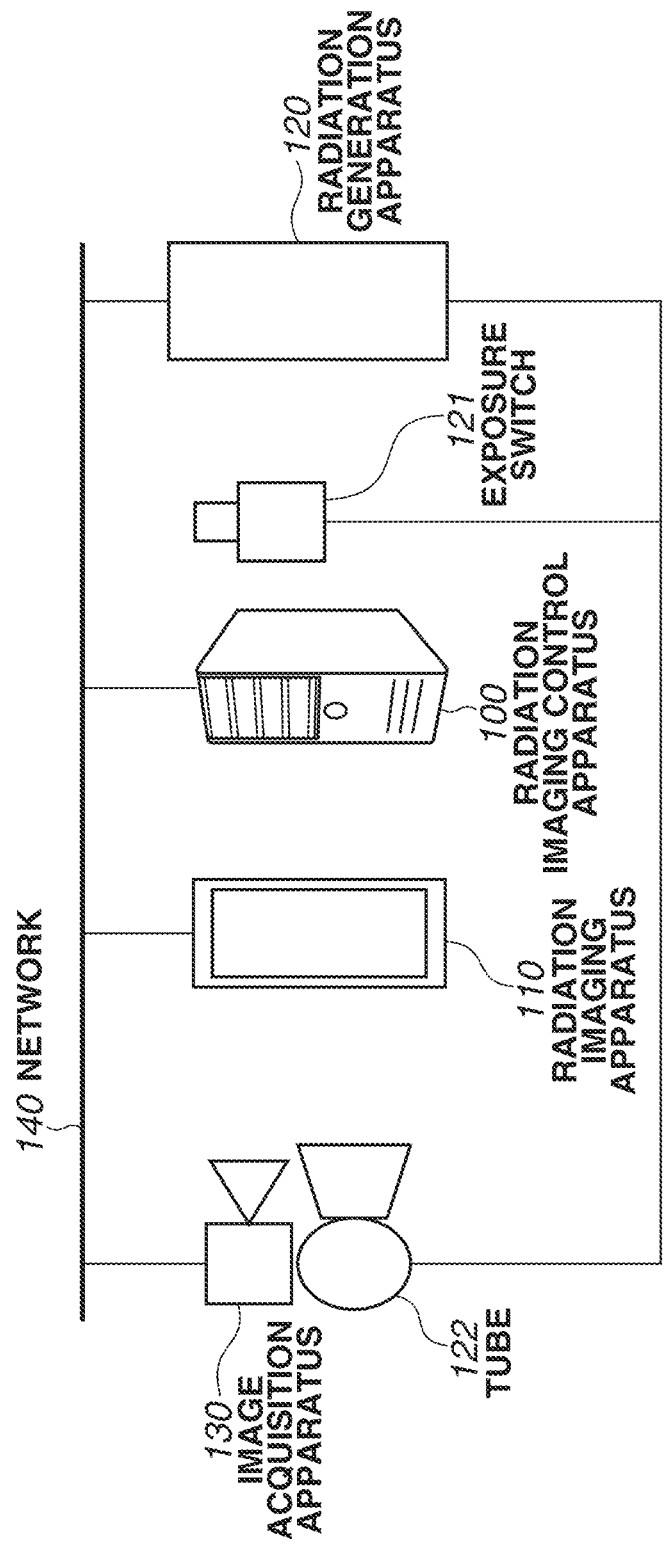
FIG. 1 illustrates a system configuration of a radiation imaging system according to a first exemplary embodiment.
Figure 2:
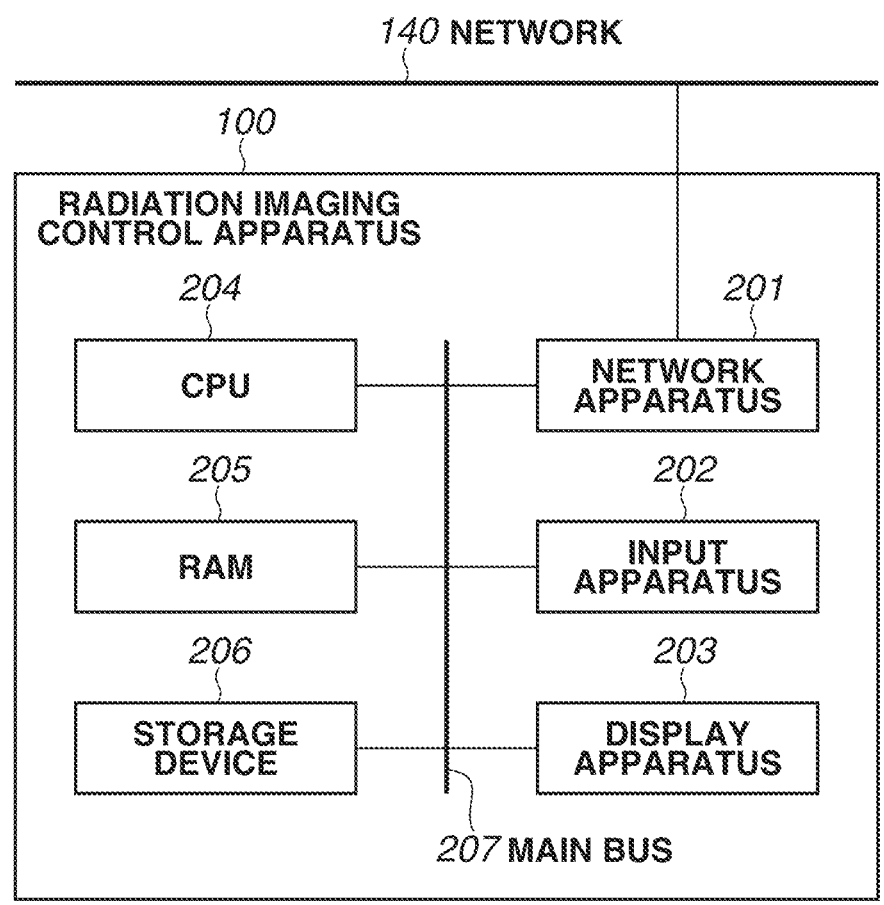
FIG. 2 illustrates a hardware configuration of a radiation imaging control apparatus according to the first exemplary embodiment.

FIG. 1 illustrates an example of an overall configuration of the radiation imaging system according to the present exemplary embodiment. The radiation imaging system includes a radiation imaging control apparatus 100, a radiation imaging apparatus 110, a radiation generation apparatus 120, and an image acquisition apparatus 130 which are all connected with each other via a network 140. The network 140 may be either a wire lined network or a wireless network.

The radiation imaging control apparatus 100 includes an information processing apparatus such as a computer which communicates with the radiation imaging apparatus 110 via the network 140 to control radiation image capturing. The radiation imaging control apparatus 100 communicates with the radiation generation apparatus 120 via the network 140 to acquire information about the radiation emission from the radiation generation apparatus 120. The radiation imaging control apparatus 100 further communicates with the image acquisition apparatus 130 to control the image acquisition apparatus 130 and acquire captured images captured by the image acquisition apparatus 130. Some of components of the radiation imaging control apparatus 100 may be an identical apparatus.

The radiation imaging apparatus 110 enters a state ready for radiation image capturing, in which a radiation image is enabled according to an instruction from the radiation imaging control apparatus 100. The radiation imaging apparatus 110 then performs radiation image capturing in synchronization with the radiation generation apparatus 120 and generates radiation images based on radiation emitted from the radiation generation apparatus 120. The number of radiation imaging apparatuses 110 is not limited to one, and a plurality of radiation imaging apparatuses 110 is also applicable.

In response to receiving a radiation emission instruction issued using an exposure switch 121, the radiation generation apparatus 120 generates radiation from a tube 122 based on an irradiation condition set via an input apparatus which receives a user operation, such as an operation panel.

The image acquisition apparatus 130 captures an image of a subject according to an instruction from the radiation imaging control apparatus 100 to acquire captured images. According to the present exemplary embodiment, the image acquisition apparatus 130 acquires captured images captured by using an optical camera. The present exemplary embodiment will be described below on the premise that the image acquisition apparatus 130 attached to the tube 122 performs image capturing in the radiation generation direction of the tube 122. More specifically, an image capturing range includes at least a region overlapping with a radiation image capturing range. However, the position at which the image acquisition apparatus 130 is attached is not limited to the tube 122, and there is no limitation on the installation position as long as foreign matters of the subject can be captured. For example, as the image acquisition apparatus 130, an indoor camera may be installed on the ceiling of a photographing room. FIG. 2 illustrates an example of a hardware configuration of the radiation imaging control apparatus 100 included in the radiation imaging system according to the present exemplary embodiment.

The radiation imaging control apparatus 100 includes a network apparatus 201 which connects to the network 140, and an input apparatus 202 which receives a user operation, such as a keyboard. The radiation imaging control apparatus 100 further includes a display apparatus 203, such as a liquid crystal display (LCD), which displays operation screens and radiation images and a Central Processing Unit (CPU) 204 which controls the entire apparatus. The radiation imaging control apparatus 100 also includes a Random Access Memory (RAM) 205 which provides a work space for the CPU 204, and a storage device 206 which stores various control programs, radiation images received from the radiation imaging apparatus 110, and captured images received from the image acquisition apparatus 130. Apparatuses included in the radiation imaging control apparatus 100 are connected with the main bus 207 and are capable of transmitting and receiving data to/from each other.

While the input apparatus 202 and the display apparatus 203 are described as separate apparatuses, these apparatuses may be integrated into one apparatus having, for example, a touch panel.

Figure 3:
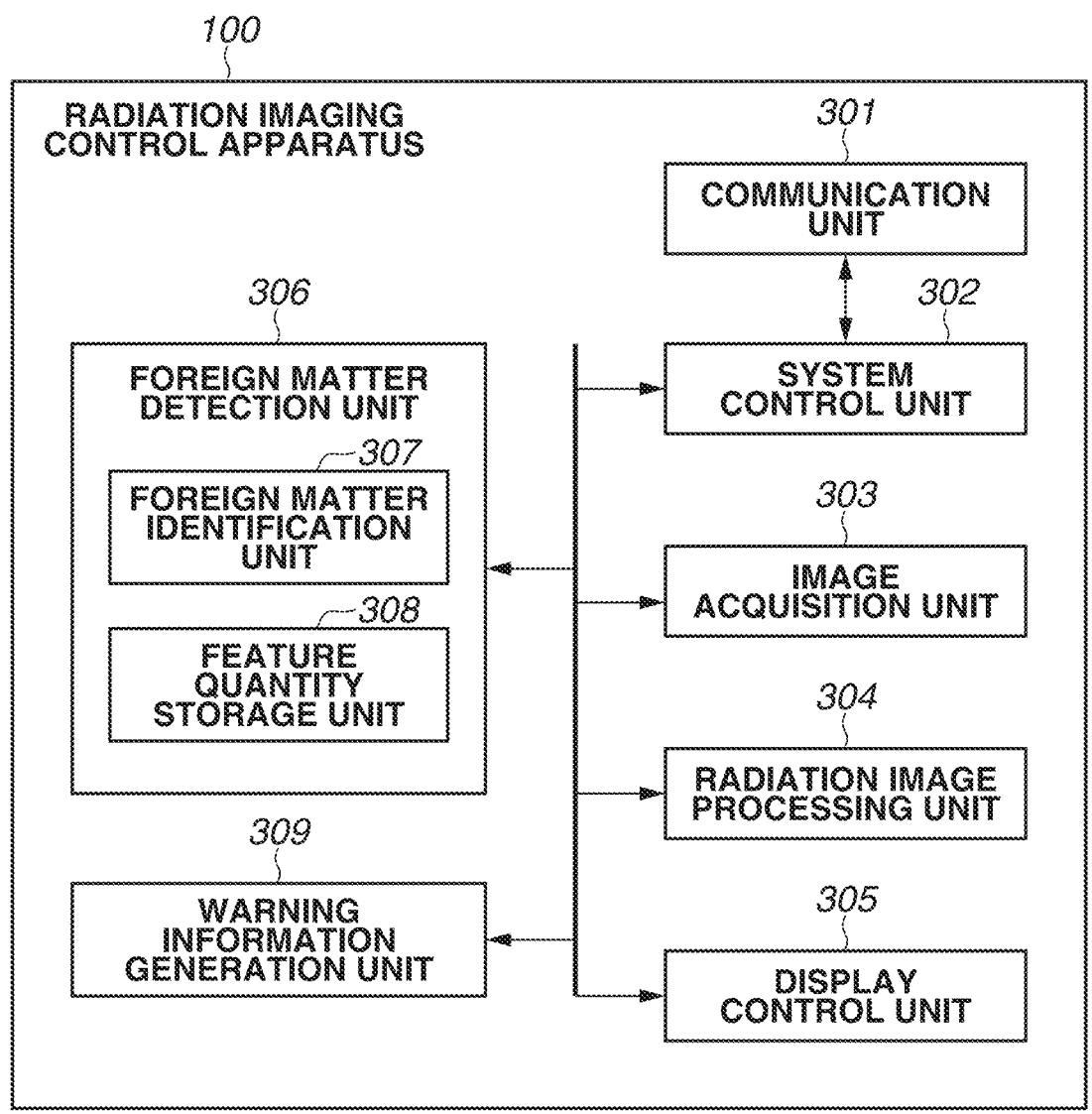
FIG. 3 illustrates a software configuration of the radiation imaging control apparatus according to the first exemplary embodiment.

FIG. 3 illustrates an example of a software configuration of the radiation imaging control apparatus 100 included in the radiation imaging system according to the present exemplary embodiment.

Each function unit illustrated in FIG. 3 is implemented by the CPU 204 in the radiation imaging control apparatus 100 loading a control program stored in the storage device 206 into the RAM 205 and then executing the program.

The radiation imaging control apparatus 100 includes a communication unit 301, a system control unit 302, an image acquisition unit 303, a radiation image processing unit 304, a display control unit 305, a foreign matter detection unit 306, and a warning information generation unit 309.

The communication unit 301 is software that controls the network apparatus 201 to perform communication.

The system control unit 302 controls the image acquisition apparatus 130, acquires information about radiation emission of the radiation generation apparatus 120 and imaging information for the radiation imaging apparatus 110, and manages the status of each apparatus via the communication unit 301. The system control unit 302 is a program that implements basic functions of the radiation imaging control apparatus 100 and controls the operation of each unit.

The image acquisition unit 303 acquires radiation images from the radiation imaging apparatus 110 and captured images from the image acquisition apparatus 130 via the communication unit 301.

The radiation image processing unit 304 processes radiation images acquired via the system control unit 302 to generate images to be used on the radiation imaging control apparatus 100.

The display control unit 305 displays an image generated by the radiation image processing unit 304 via the display apparatus 203.

The display control unit 305 further displays a notification based on warning information generated by the warning information generation unit 309 via the display apparatus 203. Here, the notification based on the warning information displayed by the display control unit 305 may be in any form, for example, a voice message or an alert sound, as long as the notification prompts the user for confirmation.

The display control unit 305 reflects processing to the image specified by the system control unit 302 based on an operation from the input apparatus 202, and changes the screen display on the display apparatus 203.

The foreign matter detection unit 306 detects a foreign matter in a captured image acquired from the image acquisition apparatus 130 by the image acquisition unit 303.

The foreign matter detection unit 306 includes a foreign matter identification unit 307 and a feature quantity storage unit 308. In a case where the foreign matter identification unit 307 identifies, based on machine learning, a foreign matter which is likely to appear in a radiation image in captured images, the feature quantity storage unit 308 stores a feature quantity for foreign matter identification from captured images that have been subjected to learning so that the foreign matter identification unit 307 is enabled to identify foreign matters. The foreign matter identification unit 307 recognizes a foreign matter in a captured image by using the feature quantity for foreign matter identification stored in the feature quantity storage unit 308, with respect to captured images. More specifically, the foreign matter detection unit 306 includes the foreign matter identification unit 307 that identifies a foreign matter by using a machine learning algorithm.

Specific methods used for machine learning according to the present exemplary embodiment is not specifically limited. For example, the foreign matter identification unit 307 may perform foreign matter identification by using ResNet as Convolutional Neural Network (CNN) architecture or by combining a plurality of machine learning techniques. The configuration of the foreign matter detection unit 306 is not limited as long as foreign matters are detectable from captured images using a captured image acquired from the image acquisition apparatus 130 by the image acquisition unit 303.

Here, a description will be provided of a configuration in which a CNN is used as a discriminator in the foreign matter identification unit 307 of the foreign matter detection unit 306. The discriminator based on machine learning including the CNN includes a learning phase for performing the learning of a discriminator and an inference phase for performing the inference by using the learned discriminator.

A configuration of the discriminator using the CNN will be described below. In the learning phase, the foreign matter identification unit 307 performs learning of the discriminator to identify foreign matters which are likely to appear in a radiation image. The CNN is classified into supervised learning in machine learning techniques. In supervised learning, learning is performed by using training data including a pair of a learning image with which learning is performed and a correct answer image indicating information about a correct answer region on the learning image. In the present specification, a correct answer image corresponds to each foreign matter which is likely to appear in a radiation image, and each foreign matter is referred to as a class. The output of the discriminator that discriminates a class is roughly classified into extraction for discriminating pixels of a class (foreign matter) discriminated on an image and sorting for discriminating the class of a foreign matter existing on the image. The use of a Softmax function for the output layer enables obtaining the output of the discriminator as a likelihood. More specifically, the foreign matter identification unit 307 outputs an identification result as a likelihood.

In the present invention, the above-described model and network structure are to be considered as examples, and the discriminator used in the foreign matter identification unit 307 may be configured based on other machine learning techniques or rule-based techniques.

Upon completion of the learning of the discriminator in the learning phase, the foreign matter identification unit 307 stores the feature quantity for detecting the foreign matter for which learning has been performed in the feature quantity storage unit 308. The learning phase of the discriminator included in the foreign matter identification unit 307 may be ended based on the number of times specified by the user. Alternatively, a learning end condition may be predetermined based on overlearning determination and/or the determination for early stopping and the like. A plurality of classes corresponding to a different one of a plurality of foreign matters may be learned by the discriminator, or the respective foreign matters may be learned by a different discriminator. When the foreign matters are learned by a plurality of discriminators, feature quantities for identifying the plurality of foreign matters are stored in the feature quantity storage unit 308.

In the inference phase, the foreign matter identification unit 307 identifies the foreign matters by using the feature quantities stored in the feature quantity storage unit 308. Both phases may be executed by different apparatuses. Any apparatus configuration is applicable as long as the feature quantities for foreign matter identification generated in the learning phase can be acquired in performing the inference in the inference phase.

When an output result of the discriminator in the foreign matter identification unit 307 is a likelihood, the foreign matter detection unit 306 determines whether a foreign matter is present, for example, on a captured image acquired by the image acquisition unit 303 through threshold value processing. In other words, the likelihood is a reliability for an identification result made by the discriminator based on machine learning by the foreign matter identification unit 307. Thus, the foreign matter detection unit 306 presets a threshold value and detects a foreign matter corresponding to a class having a predetermined threshold value or larger as a foreign matter that is present on the captured image. More specifically, the foreign matter detection unit 306 detects a foreign matter having a likelihood greater than or equal to a threshold value out of output results obtained by the foreign matter identification unit 307.

In a case where the foreign matter detection unit 306 detects a foreign matter, the warning information generation unit 309 generates warning information representing the detection of a foreign matter. Subsequently, the warning information generation unit 309 instructs the display control unit 305 to display the generated warning information on the screen. Details will be described below in conjunction with a configuration drawing of the warning screen of the warning information generation unit 309.

The radiation imaging control apparatus 100 includes the image acquisition unit 303 that acquires the captured image of a target patient who is a subject, and the foreign matter detection unit 306 that detects a foreign matter which is likely to appear in a radiation image, in the captured image acquired by the image acquisition unit 303. The radiation imaging control apparatus 100 includes the warning information generation unit 309 that generates, in a case where the foreign matter detection unit 306 detects a foreign matter, warning information regarding radiation image capturing based on the detected foreign matter, and the display control unit 305 that displays a notification based on the warning information generated by the warning information generation unit 309.

Figure 5A:
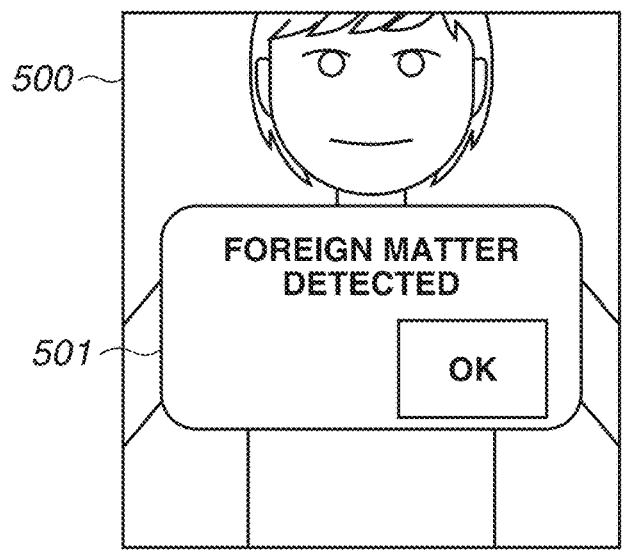
FIG. 5A is a schematic view illustrating a warning screen of the radiation imaging control apparatus according to the first exemplary embodiment.
Figure 5B:
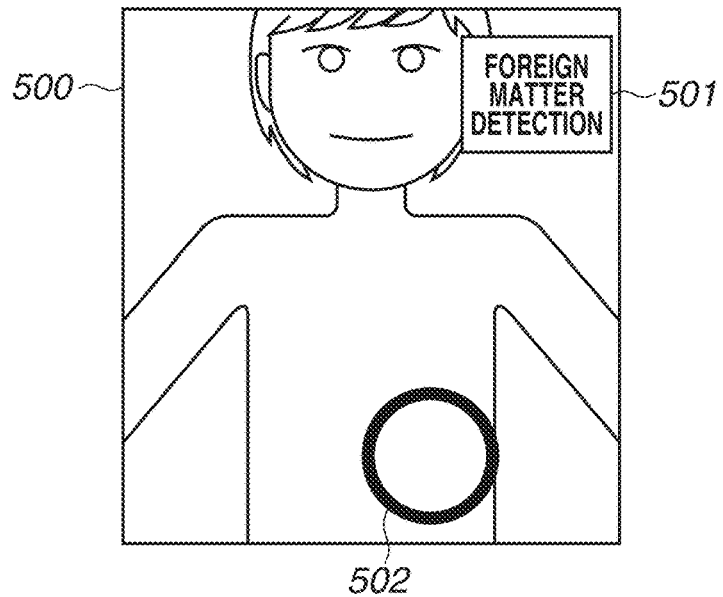
FIG. 5B is a schematic view illustrating a warning screen of the radiation imaging control apparatus according to the first exemplary embodiment.

FIG. 4 illustrates a display processing method performed by the radiation imaging control apparatus 100 when an image of the target patient is captured, according to the present exemplary embodiment. FIGS. 5A and 5B each illustrate a configuration regarding a warning image display.

FIG. 4 is a flowchart illustrating notification display processing by the radiation imaging control apparatus 100.

In step S401, the system control unit 302 shifts the radiation imaging control apparatus 100 to a state for starting an inspection based on a user operation. More specifically, the system control unit 302 transmits, to the radiation imaging apparatus 110 via the communication unit 301, an instruction to prepare for image capturing based on the imaging condition for the target patient for who an inspection instruction is issued by a user operation. When the radiation imaging apparatus 110 completes the imaging preparation, the radiation imaging apparatus 110 transmits a preparation completion notification to the radiation imaging control apparatus 100 in response to the instruction. After the radiation imaging control apparatus 100 receives the preparation completion notification, the system control unit 302 shifts the radiation imaging control apparatus 100 to the state for starting an inspection and so that an operation in step S406 (described below) is received. The system control unit 302 transmits an instruction to start image capturing to the image acquisition apparatus 130 via the communication unit 301. After reception of the instruction to start image capturing, the image acquisition apparatus 130 successively transmits captured images acquired by itself to the radiation imaging control apparatus 100.

Operations in steps S403 to S405 are performed by the system control unit 302 until the operation in step S406 is performed or the inspection is determined to be canceled by a user operation.

In step S402, the image acquisition unit 303 displays the captured image acquired from the image acquisition apparatus 130 via the communication unit 301 on the display apparatus 203 via the display control unit 305.

In step S403, the foreign matter detection unit 306 detects a foreign matter in the captured image based on the captured image acquired via the image acquisition unit 303.

If the foreign matter detection unit 306 detects a foreign matter in the captured image (YES in step S403), the processing proceeds to step S404. In step S404, the warning information generation unit 309 generates warning information.

In step S405, the display control unit 305 issues a notification based on the warning information, on the display apparatus 203.

If the foreign matter detection unit 306 detects no foreign matter (NO in step S403), the radiation imaging control apparatus 100 does not generate warning information. More specifically, the radiation imaging control apparatus 100 skips the operations in steps S404 and S405.

In step S406, the user presses the exposure switch 121 of the radiation generation apparatus 120 to start radiation image capturing. When radiation image capturing is started, the radiation generation apparatus 120 generates radiation from the tube 122, the radiation that has passed through the target patient is notified to the radiation imaging apparatus 110. The radiation imaging apparatus 110 then generates a captured radiation image. Subsequently, the radiation imaging apparatus 110 transmits the captured radiation image to the radiation imaging control apparatus 100. In parallel with the above-described processing, the radiation generation apparatus 120 transmits the radiation emission information regarding the radiation image capturing to the radiation imaging control apparatus 100.

FIGS. 5A and 5B are schematic views illustrating notifications displayed on the radiation imaging control apparatus 100 according to the present exemplary embodiment.

A display screen 500 displayed by the display apparatus 203 includes the captured image that is acquired from the image acquisition apparatus 130 and displayed on the display apparatus 203 in step S402. The actual captured image includes an object in the image capturing range of the image acquisition apparatus 130 due to, for example, the presence of the radiation imaging apparatus 110 behind the target patient. However, the display screen 500 displays only body information for the target patient for simplification. Unless otherwise noted, for captured images and images related to the captured images to be subsequently displayed on the display screen 500, only the body information for the target patient is represented.

Figure 5C:
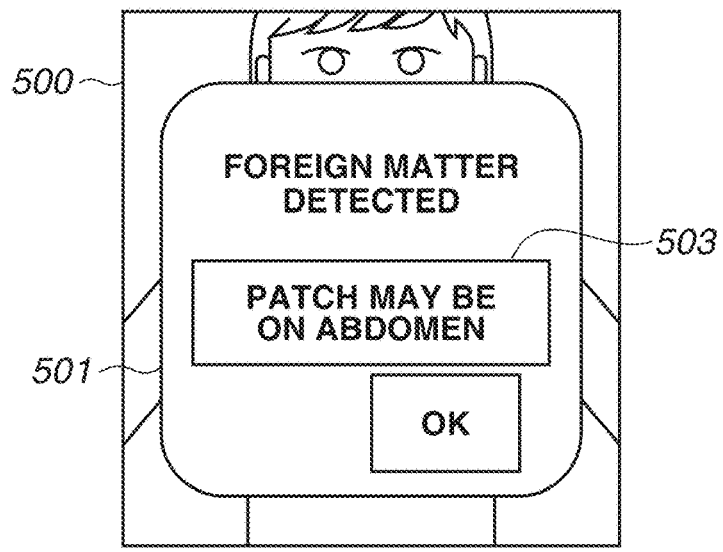
FIG. 5C is a schematic view illustrating a warning screen of the radiation imaging control apparatus according to the first exemplary embodiment.

A notification 501 in each of FIGS. 5A, 5B, and 5C is based on the warning information indicating the presence of a foreign matter generated by the warning information generation unit 309 in step S404. Referring to FIG. 5A, in a case where the foreign matter detection unit 306 detects a foreign matter, a warning text is displayed on the captured image 500 as the notification 501 to prompt the user for confirmation. However, the screen configuration is not limited as long as the presence of a foreign matter can be presented to the user. For example, as in the screen configuration in FIG. 5B, the display control unit 305 may display the notification 501 and foreign matter detection information 502 for indicating a region on the captured image where an object is determined to be a foreign matter. This enables the user to immediately grasp the fact that a foreign matter has been detected and the position of the foreign matter on the display screen 500. In the display screen 500, the display control unit 305 may display the warning information (notification) 501 and foreign matter detailed information 503 representing foreign matter information about a foreign matter determined to be a foreign matter on the captured image, as in the configuration in FIG. 5C. The combination of the foreign matter detection information 502 and the foreign matter detailed information 503 enables the user to grasp the foreign matter information to be confirmed by the user, and the foreign matter detection information 502 enables the user to confirm the grasped foreign matter at the position of the foreign matter.

More specifically, the warning information generation unit 309 generates warning information indicating a foreign matter detected by the foreign matter detection unit 306 and the position of the foreign matter.

The above-described display methods may be combined, or only a part of the configuration may be displayed on the display screen 500.

As described above, in the radiation imaging control apparatus 100 according to the first exemplary embodiment, the foreign matter detection unit 306 detects a foreign matter which is likely to appear in a captured radiation image, with respect to a captured image acquired before the radiation image acquisition, and the display control unit 305 issues a warning-based notification on the display apparatus 203. This notification enables the user to notice a foreign matter, thus preventing undesired radiation re-imaging and accordingly preventing ineffective exposure to the target patient.

First Modification

Processing to be performed in a case where a plurality of foreign matters is detected by the foreign matter detection unit 306 will be described below with reference to FIG. 4. In step S403, the foreign matter detection unit 306 detects a plurality of foreign matters. The foreign matter identification unit 307 in the foreign matter detection unit 306 may identify a foreign matter as a class of a plurality of different discriminators, or may identify a plurality of foreign matters as different classes of an identical discriminator.

In a case where the discriminator in the foreign matter identification unit 307 identifies foreign matters in different image regions on a captured image, the foreign matter detection unit 306 performs threshold value processing on the likelihoods corresponding to respective foreign matters by the foreign matter identification unit 307 to detect foreign matters corresponding to the classes having the likelihoods equal to or larger than a threshold value. In a case where the foreign matter identification unit 307 detects a plurality of foreign matters in an image region including the same image region on the captured image, the foreign matter identification unit 307 compares the likelihoods of the classes corresponding to the plurality of foreign matters to detect the foreign matter corresponding to the class having the highest likelihood. Alternatively, in a case where the area of the same image region on the captured image is a constant value or less, or the ratio of the image region indicating a foreign matter to the detected foreign matter region is equal to or less than a constant value, the foreign matter identification unit 307 may detect the results of the identification of the plurality of foreign matters by the discriminator, as respective foreign matters.

In step S404, the warning information generation unit 309 generates the notification 501 so that foreign matters corresponding to a plurality of pieces of foreign matter information acquired from the foreign matter detection unit 306 are individually identifiable. For example, in a case where the number of foreign matters detected by the foreign matter detection unit 306 is too large to display notifications based on respective pieces of warning information on the same display screen 500, the warning information generation unit 309 generates the notifications 501 for respective foreign matters and displays the notifications 501 in a switchable manner. Alternatively, in a case where the detected foreign matters can be displayed on the display screen 500, the warning information generation unit 309 generates warning information to display a plurality of pieces of foreign matter information as warning information on the same display screen. In a case where the warning information generation unit 309 causes the display control unit 305 to display a plurality of pieces of foreign matter information on the same display screen, the warning information generation unit 309 may perform, for example, display processing of changing the display density and/or color so that each individual foreign matter is identifiable from other ones.

In step S405, the display control unit 305 displays the warning information acquired from the warning information generation unit 309 on the display screen 500. The display control unit 305 identifiably displays each of the plurality of foreign matters. The display control unit 305 displays a plurality of foreign matters in a switchable manner and displays a plurality of pieces of foreign matter information on the same display screen. The display performed by the display control unit 305 is not limited thereto. For example, foreign matters to be checked may be displayed in list form. In a case where a plurality of foreign matters is present, the display control unit 305 may display a check list (items) in which whether the user has checked is input.

The present modification enables the user to grasp the presence or absence and positions of foreign matters and foreign matter information even if a plurality of foreign matters is detected by the foreign matter detection unit 306. This enables prevention of ineffective exposure due to undesired radiation re-imaging.

Second Modification

In the first exemplary embodiment, a configuration has been described in which the image acquisition apparatus 130 is provided with an optical camera, and the foreign matter detection unit 306 performs foreign matter detection targeting captured images by using optical images as acquired captured images. However, the foreign matter detection unit 306 may perform foreign matter detection by using a near-infrared camera on the image acquisition apparatus 130 and near-infrared light images as acquired captured images, or by using captured images captured by the optical camera together with the captured images captured by the near-infrared camera. More specifically, captured images acquired by the image acquisition unit 303 are captured images captured by at least either one of the optical camera and the near-infrared camera.

A description will be provided below of a configuration in a case where the foreign matter identification unit 307 in the foreign matter detection unit 306 performs foreign matter identification by using a CNN-based discriminator, as a method for detecting foreign matters by using a plurality of captured images.

In a case where the foreign matter identification unit 307 in the foreign matter detection unit 306 performs foreign matter identification based on machine learning such as a CNN, training data is to be used as described above. In the above descriptions, the learning of the discriminator in the foreign matter identification unit 307 is performed by using training data including a pair of an image captured by the optical camera and a correct answer image indicating correct answer region information corresponding to the class indicating the foreign matter as a correct answer image, and a feature quantity for identifying a foreign matter generated in the learning is stored in the feature quantity storage unit 308. In a case where a captured image includes a plurality of images captured by the optical camera and/or the near-infrared camera, for example, a method for separately performing the learning of two different discriminators is applicable. One discriminator is trained based on training data including a pair of an image captured by the optical camera and a correct answer image indicating correct answer region information, such as training data for the above-described discriminator. The other discriminator is trained based on training data including a pair of an image captured by the near-infrared camera and a correct answer image indicating correct answer region information. The use of the training data including images captured by the optical camera and the training data including images captured by the near-infrared camera enables the discriminators to learn different features. Comparing results of foreign matter identification made by the respective discriminators enables prevention of foreign matter detection failure, thus guaranteeing the consistency in foreign matter identification.

There is another method for performing the learning of the discriminator by using images captured by the optical camera and images captured by the near-infrared camera as learning images. In this method, discriminator is trained with these images as correct answer images corresponding to the correct answer region. By using images captured by the optical camera and images captured by the near-infrared camera as learning images at the same time, feature quantities in which the relation between captured images is reflected can be generated through the learning.

While a near-infrared camera has been described above as an example of an infrared camera, the wavelength band to be acquired by the infrared camera is not limited to near-infrared light.

The information to be provided to the foreign matter detection unit 306 is not limited to the above-described information. The foreign matter detection unit 306 may be configured to receive input of images captured by other imaging apparatuses capable of acquiring image information that cannot be acquired by the optical camera, or information other than captured images, such as information about a metal detector.

Third Modification

A description has been provided of a configuration in which images captured by the optical camera and the near-infrared camera are input, and then the foreign matter detection unit 306 detects foreign matters, in the second modification. In a third modification, a description will be provided of a configuration in which at least either one of the captured image to be detected by the foreign matter detection unit 306 and the feature quantity of a foreign matter discriminator is adjusted in accordance with the status of the target patient as a subject.

For example, in radiation image capturing, the status of the image capturing range may be different for individual target patients. For example, the difficulty in detecting a foreign matter from a captured image and the feature quantity for detecting a foreign matter are assumed to be different between an image captured with the subject in clothes and an image captured with the subject without clothes. Therefore, in the present modification, the user inputs or determines the status of the target patient to adjust at least either one of the input to the foreign matter detection unit 306, which detects a foreign matter, and the feature quantity to be used by the foreign matter identification unit 307 in the foreign matter detection unit 306. In a case where the target patient wears clothes, it is more difficult to detect a foreign matter from an image captured by the optical camera than in a case where the target patient does not wear clothes. In a case where the target patient wears clothes, at least an image captured by the near-infrared camera is input to the foreign matter detection unit 306. Regarding the feature quantity to be acquired by the foreign matter identification unit 307 in the foreign matter detection unit 306 from the feature quantity storage unit 308, the feature quantity generated by the learning of the training data including at least an image captured by the near-infrared camera is selected.

The present modification enables the foreign matter detection unit 306 to perform foreign matter detection suitable for the status of the target patient, thus preventing foreign matters from appearing in an image.

Second Exemplary Embodiment

A second exemplary embodiment of the present invention will be described below.

In the configuration according to the first exemplary embodiment, the foreign matter detection unit 306 detects a foreign matter which is likely to appear in a captured radiation image, from a captured image acquired by the image acquisition unit 303. However, if the user wears an object to be detected as a foreign matter in a captured image, it may be desirable not to detect a foreign matter or issue a notification in a range that does not appear in a radiation image.

In general, the radiation emitted from the radiation generation apparatus 120 is radiated to a limited region on the subject by a collimator. This region is referred to as an irradiation field. In a case where the irradiation field is the chest of the target patient, and if, for example, a transdermal therapeutic patch put on the arm appears in a captured image, it is desirable not to detect the transdermal therapeutic patch put on the arm as a foreign matter or issue a notification because the irradiation field is within a range that does not appear in a radiation image. If a foreign matter is detected in a range that does not appear in a radiation image, and a warning is displayed to the user, the user needs to check the foreign matter although the object does not affect radiation image capturing. This may increase the user's time and labor in operations.

Thus, the configuration of the second exemplary embodiment includes additional processing for generating irradiation field information by the radiation imaging control apparatus 100 and additional processing of foreign matter detection by the foreign matter detection unit 306. Only differences of the present exemplary embodiment from the first exemplary embodiment will be described below with reference to FIGS. 6 and 7.

Figure 6:
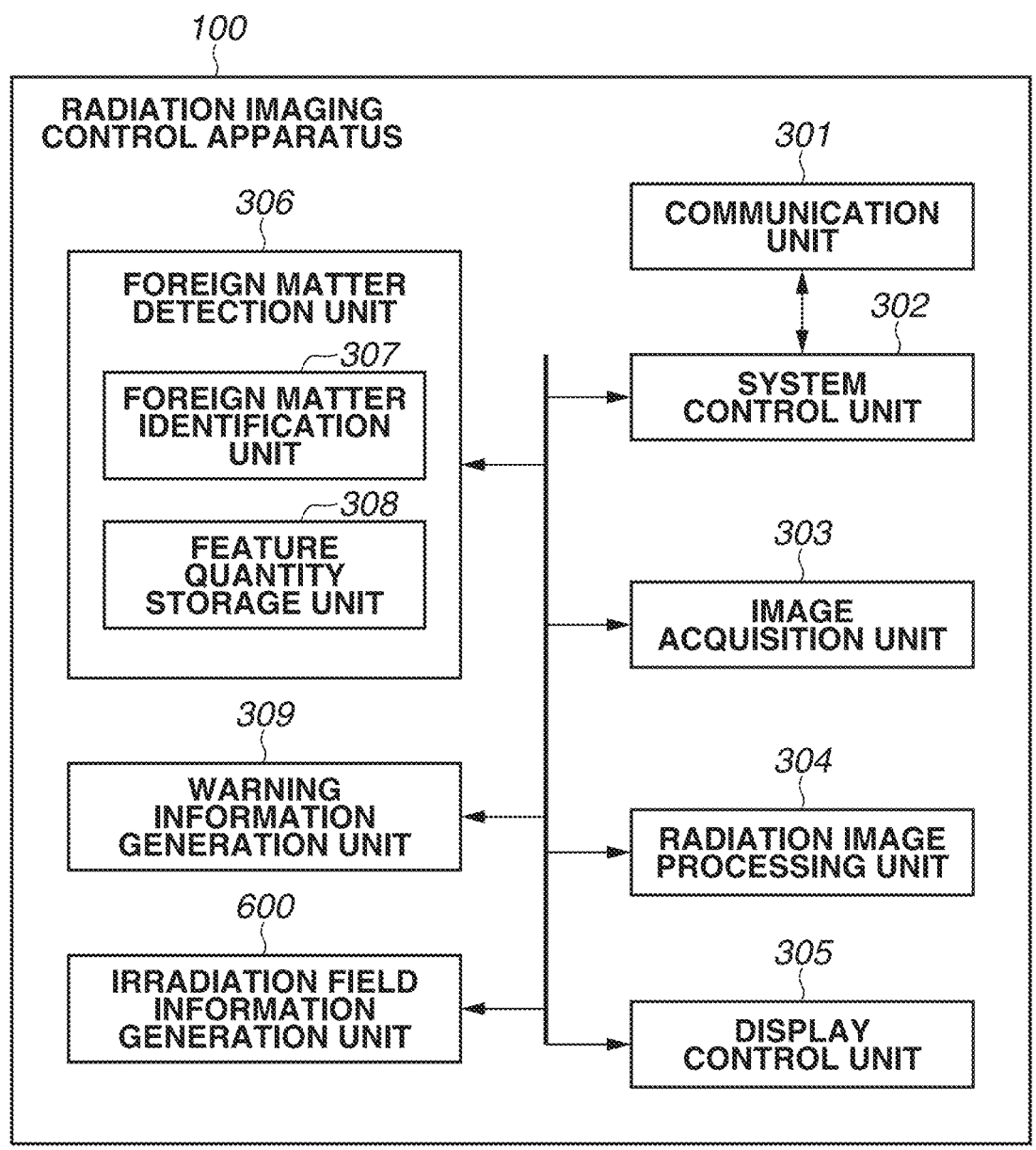
FIG. 6 illustrates a software configuration of the radiation imaging control apparatus according to the second exemplary embodiment.

FIG. 6 illustrates an example of a software configuration of the radiation imaging control apparatus 100. The radiation imaging control apparatus 100 according to the present exemplary embodiment includes an irradiation field information generation unit 600 in addition to the configuration according to the first exemplary embodiment. The irradiation field information generation unit 600 generates the irradiation field information representing positional information for the irradiation field region in a captured image. In the present exemplary embodiment, for example, the irradiation field information generation unit 600 performs image analysis on luminance variations in captured images, when the irradiation field lamp of the tube 122 is ON, acquired from the image acquisition apparatus 130, and generates the irradiation field information. More specifically, after the irradiation field lamp of the tube 122 turns OFF, the radiation imaging control apparatus 100 keeps storing the irradiation field information immediately before the irradiation field lamp turns OFF, in the storage device 206.

More specifically, the radiation imaging control apparatus 100 includes the irradiation field information generation unit 600 which detects, from a captured image, the position of the irradiation field provided by the radiation generation apparatus 120, and generates the irradiation field information. The foreign matter detection unit 306 detects foreign matters from the image region corresponding to the irradiation field information generated by the irradiation field information generation unit 600 out of the captured image acquired by the image acquisition unit 303.

There is no limitation on the detection method as long as the positional information for the irradiation field region can be acquired by the irradiation field information generation unit 600. For example, diaphragm information for the tube 122 may be pre-acquired from the radiation generation apparatus 120 and the irradiation field region may be calculated. Alternatively, the irradiation field region may be calculated based on machine learning such as a CNN.

Figure 7:
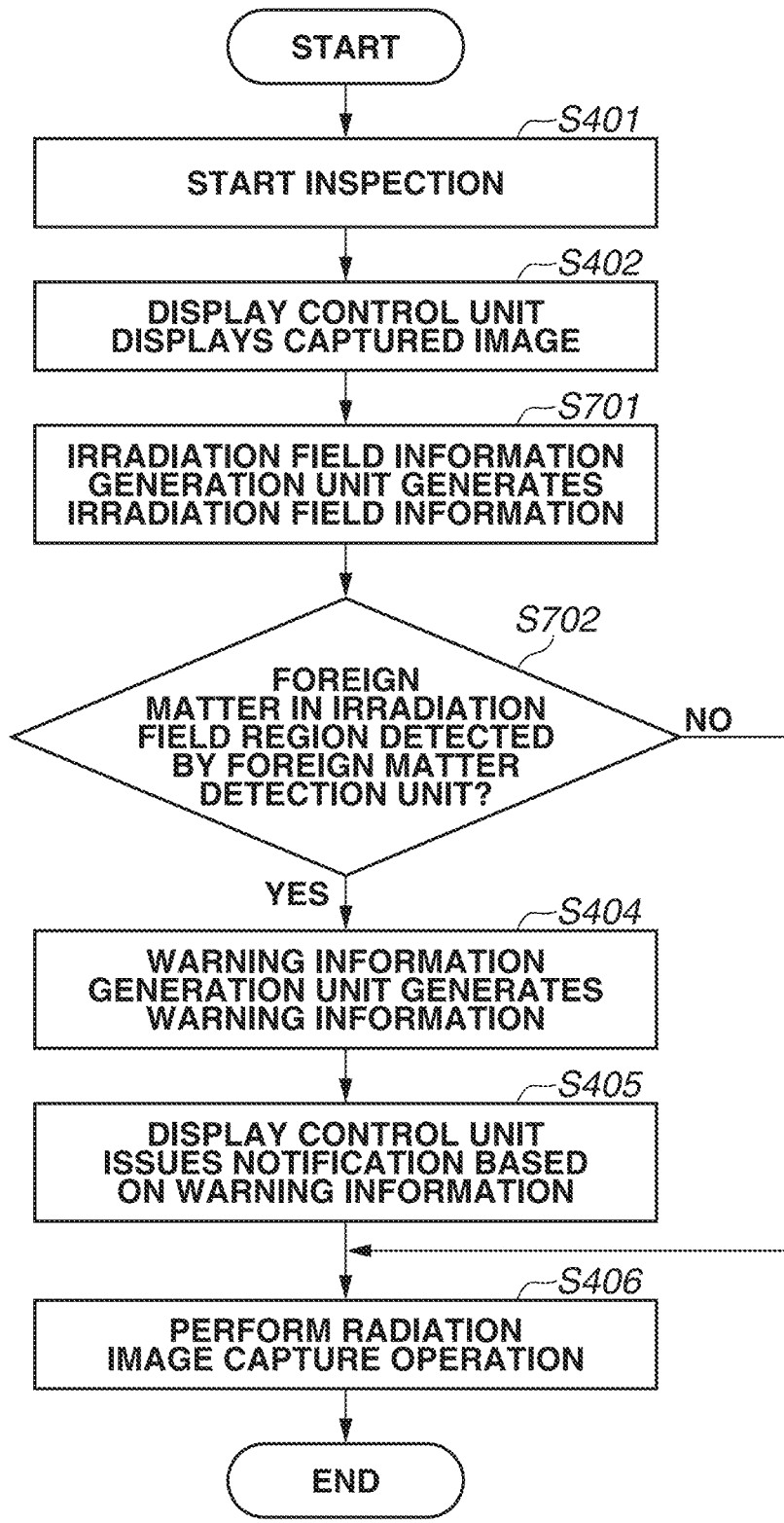
FIG. 7 is a flowchart illustrating processing of the radiation imaging control apparatus according to the second exemplary embodiment.

FIG. 7 is a flowchart illustrating processing of displaying warning information for the radiation imaging control apparatus 100 according to the present exemplary embodiment.

In step S701, the irradiation field information generation unit 600 generates the irradiation field information indicating the irradiation field region from a captured image through the above-described image analysis.

In step S702, the foreign matter detection unit 306 performs foreign matter detection processing on the image region on the captured image corresponding to the irradiation field region based on the irradiation field information generated from a captured image acquired by the image acquisition unit 303. Unlike step S403 in the first exemplary embodiment, operations in steps S404 and S405 in the subsequent stage are executed in a case where a foreign matter is detected in the image region corresponding to the irradiation field region on the captured image based on the irradiation field information through the foreign matter detection in step S702.

According to the second exemplary embodiment, when the radiation imaging control apparatus 100 starts an inspection, the irradiation field information generation unit 600 generates the irradiation field information from a captured image acquired by the image acquisition unit 303, and the foreign matter detection unit 306 displays a warning on the display apparatus 203. This warning indicates whether a foreign matter which is likely to appear in a captured radiation image exists in the image region corresponding to the irradiation field region in the irradiation field information. Accordingly, even if the foreign matter detection unit 306 detects a foreign matter which is likely to appear in a radiation image from the region not affecting image capturing, the foreign matter detection unit 306 does not display a warning, preventing the increase in the amount of trouble due to user's confirmation operations.

Third Exemplary Embodiment

The radiation images make it possible to acquire image information for the internal body of a subject which cannot be acquired with an optical image. The use of a radiation image enables identification of the position of a foreign matter, such as a fragment of glass inside the body, so that the foreign matter can be removed by a surgery based on the identified position.

In some radiation images, a foreign matter inside the body of a subject may overlap with a hard tissue such as a bone. If a foreign matter overlaps with a hard tissue on a radiation image, it becomes difficult to find the foreign matter in the radiation image, increasing the risk of overlooking. If a foreign matter is neither found nor removed by a surgery, the symptom of the subject may become serious.

Thus, the present exemplary embodiment is directed to providing an image processing apparatus that detects an abnormality in an optical image and displays abnormality information regarding the detected abnormality together with a radiation image, thus assisting the operator to find a foreign matter.

Figure 8:
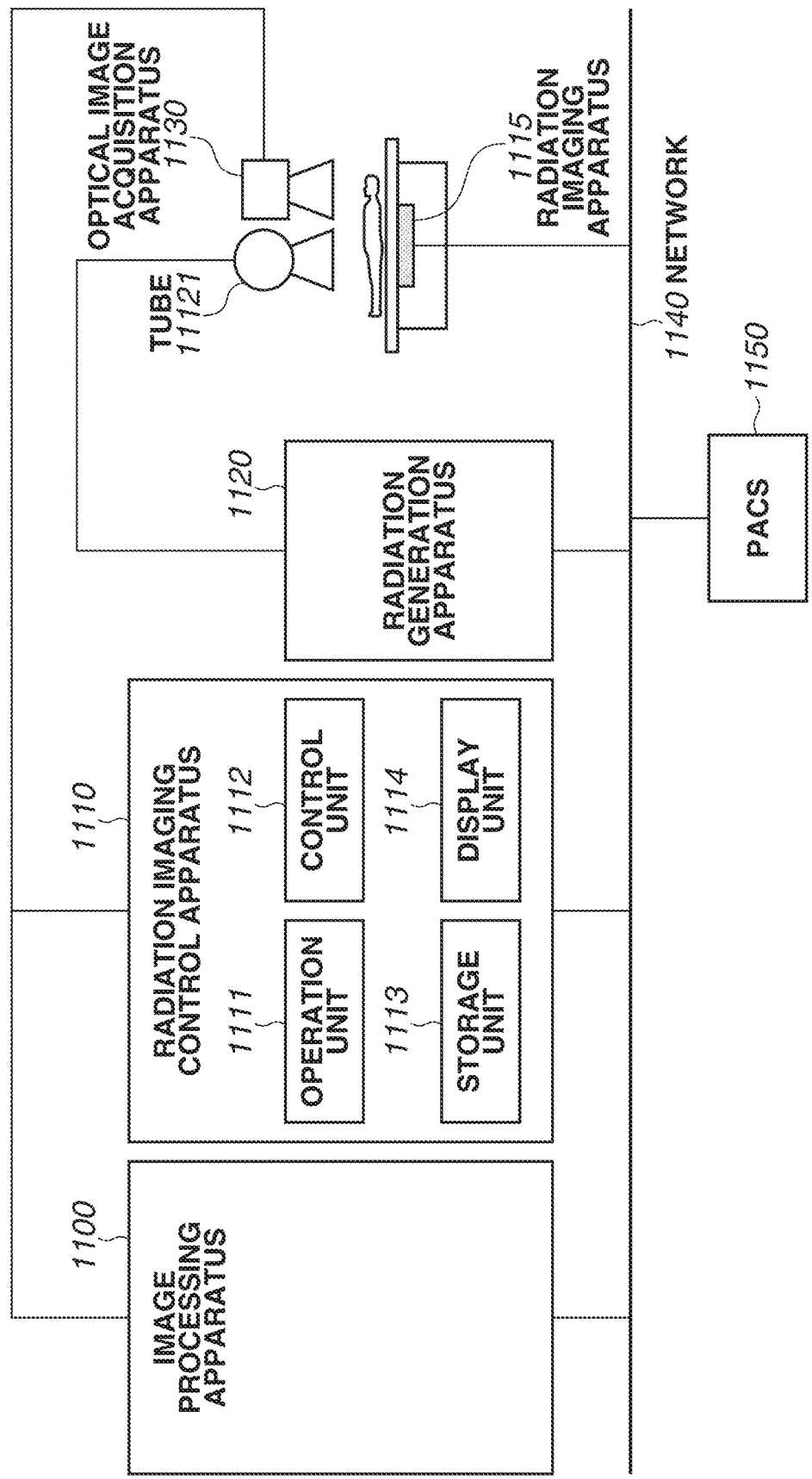
FIG. 8 illustrates a system configuration of a radiation imaging system according to a third exemplary embodiment.

FIG. 8 illustrates an example of a configuration of a radiation imaging system according to exemplary embodiments of the present invention.

The radiation imaging system includes an image processing apparatus 1100, a radiation imaging control apparatus 1110, a radiation generation apparatus 1120, and an optical image acquisition apparatus 1130 which are all connected with each other via a network 1140 including a Local Area Network (LAN) or a Wide Area Network (WAN). The network 1140 may be a wire lined network or a wireless network.

The image processing apparatus 1100 acquires an optical image optically captured by the optical image acquisition apparatus 1130, and a radiation image captured by a radiation imaging apparatus 1115. The image processing apparatus 1100 then subjects the acquired optical image to abnormality detection processing and then displays abnormality information for the detected abnormality together with the acquired radiation image. The image processing apparatus 1100 includes an information processing apparatus such as a computer. The computer includes, for example, a main control unit such as a CPU, a Read Only Memory (ROM), and a Random Access Memory (RAM). For example, the configuration of the image processing apparatus 1100 may be entirely or partially located on the cloud as long as the image processing apparatus 1100 is connected with the radiation imaging system via the network 140. The configuration of the image processing apparatus 1100 (described below) may be implemented as a part of apparatuses included in the system.

The radiation imaging control apparatus 1110 includes an information processing apparatus, such as a computer, which communicates with the radiation imaging apparatus 1115 to control radiation image capturing. The computer includes, for example, a main control unit such as a CPU, a ROM, and a RAM. The radiation imaging control apparatus 1110 includes a network apparatus which connects to the network 1140, an operation unit 1111 including a keyword and mouse which receive operations from the operator, a control unit 1112 which controls the entire system, a storage unit 1113 which stores various control programs, radiation images received from the radiation imaging apparatus 1115, and image information received from the optical image acquisition apparatus 1130. The radiation imaging control apparatus 1110 further includes a display unit 1114 such as a LCD which displays radiation images. Although the operation unit 1111 and the display unit 1114 are described as separate apparatuses, these units may be integrated into one operation unit. The radiation imaging control apparatus 1110 communicates with the radiation generation apparatus 1120 to acquire information when the radiation generation apparatus 1120 performs the radiation emission. The radiation imaging control apparatus 1110 communicates with the optical image acquisition apparatus 1130 to control the optical image acquisition apparatus 1130 and acquire optical images optically captured by the optical image acquisition apparatus 1130. A Picture Archiving and Communication Systems (PACS) 1150 is an image server. The radiation imaging control apparatus 1110 attaches inspection information to a captured radiation image and transfer the image to the PACS 1150.

The radiation imaging apparatus 1115 enters the state ready for image capturing according to an instruction from the radiation imaging control apparatus 1110, and performs radiation image capturing in synchronization with the radiation generation apparatus 1120 to generate a radiation image based on the radiation emitted by the radiation generation apparatus 1120. The number of radiation imaging apparatuses 1115 is not limited to one, and a plurality of radiation imaging apparatuses is also applicable.

The radiation generation apparatus 1120 detects a radiation emission instruction from the operator, and generates radiation from the tube 1121 based on an irradiation condition set by the operator via an operation unit for receiving operator's operations, such as a keyboard.

The optical image acquisition apparatus 1130 performs optical image capturing according to an instruction from the radiation imaging control apparatus 1110 to acquire an optical image. In the present exemplary embodiment, optical images are acquired by using an optical camera provided on the optical image acquisition apparatus 1130. In the present exemplary embodiment, the optical image acquisition apparatus 1130 is attached to the tube 1121, performs image capturing in the radiation generation direction of the tube 1121, and has an image capturing range equivalent to radiation images.

A description has been provided of an example of a radiation imaging system according to respective exemplary embodiments of the present invention. The configuration illustrated in FIG. 8 is to be considered to be merely an example and can be suitably changed. For example, in FIG. 8, various apparatuses are connected to the image processing apparatus 1100 and the radiation imaging control apparatus 1110 via the network 1140. However, the configuration of the radiation imaging system is not necessarily limited thereto. For each apparatus, a plurality of the apparatuses may be present on the network 1140.

Figure 9:
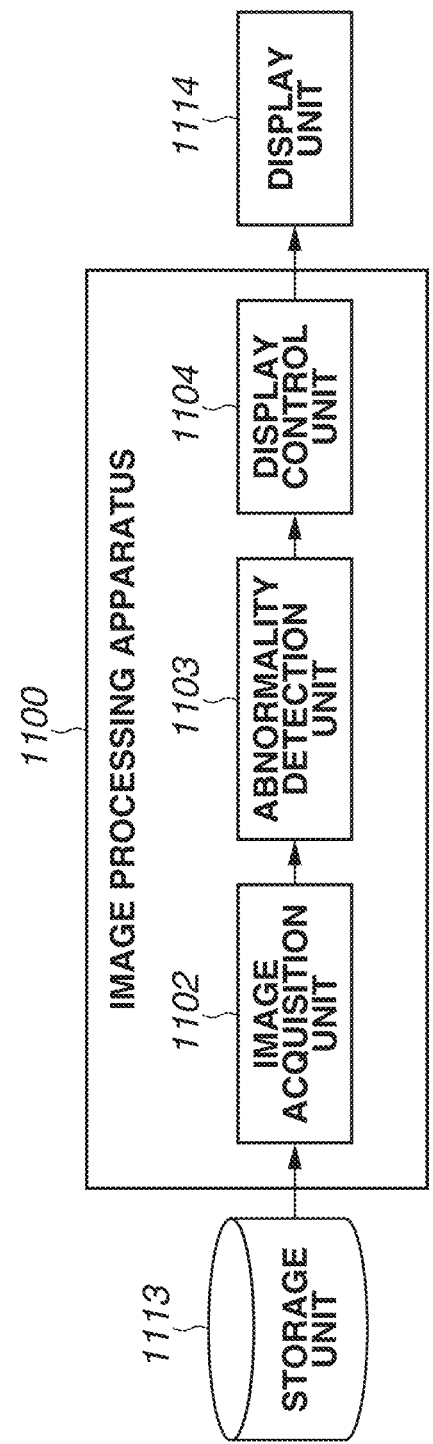
FIG. 9 illustrates a configuration of an image processing apparatus according to the third exemplary embodiment.

Components of the image processing apparatus 1100 included in the radiation imaging system and the respective functions thereof will be described below with reference to FIG. 9.

The image processing apparatus 1100 included in the radiation imaging system includes an image acquisition unit 1102 which acquires an optical image from the storage unit 1113 in the radiation imaging control apparatus 1110 and a radiation image, an abnormality detection unit 1103 which detects an abnormality in the optical image acquired by the image acquisition unit 1102, and a display control unit 1104 which causes the display unit 1114 in the radiation imaging control apparatus 1110 to display an object based on abnormality information regarding the detected abnormality together with the acquired radiation image.

The image acquisition unit 1102 acquires an optical image and a radiation image stored in the storage unit 1113. The image acquisition unit 1102 then transmits the acquired image to the abnormality detection unit 1103.

The abnormality detection unit 1103 performs abnormality detection processing on optical images out of images transmitted from the image acquisition unit 1102. In the abnormality detection processing, an abnormality is detected, for example, by using CNN as one of machine learning techniques. More specifically, the abnormality detection unit 1103 performs abnormality detection based on machine learning, which is a characterizing feature of the abnormality detection unit 1103. In abnormality detection, other deep learning techniques, other machine learning techniques, conventional rule-based image processing techniques, or a combination of these techniques may be applicable. When the abnormality detection unit 1103 detects an abnormality regarding the subject, the abnormality detection unit 1103 transmits the category of the detected abnormality, abnormality information indicating the position of the abnormality on the image, and an acquired radiation image to the display control unit 1104. More specifically, the abnormality information includes the category of the abnormality and the coordinates of the abnormality on the optical image.

The display control unit 1104 displays an object based on the abnormality information and the radiation image transmitted from the abnormality detection unit 1103 on the display unit 1114 in the radiation imaging control apparatus 1110.

More specifically, the image processing apparatus 1100 includes the image acquisition unit 1102 which acquires an optical image obtained by optically capturing an image of a subject and a radiation image of the subject obtained by performing radiation image capturing of a subject, the abnormality detection unit 1103 which detects an abnormality from the optical image acquired by the image acquisition unit 1102, and the display control unit 1104 which displays, in a case where an abnormality is detected in the optical image by the abnormality detection unit 1103, an object based on the abnormality information for the detected abnormality together with the radiation image.

Procedures for performing abnormality detection processing on an optical image along the inspection processing by the radiation imaging system illustrated in FIG. 8, and then displaying abnormality information generated based on the detected abnormality together with a radiation image will be described below with reference to FIG. 11.

Figure 10:
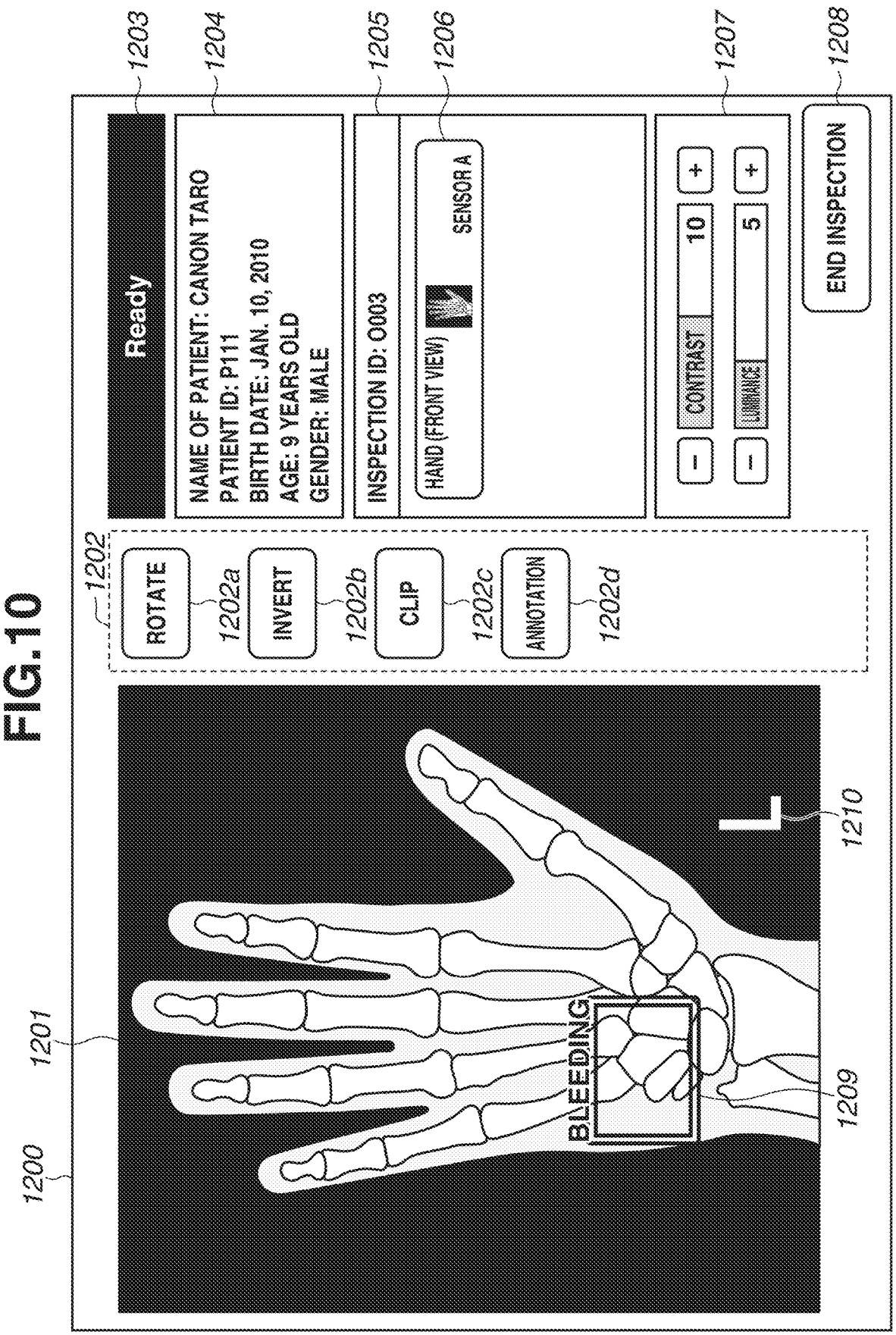
FIG. 10 illustrates a display screen of a radiation imaging control apparatus according to the third exemplary embodiment.

FIG. 10 illustrates an example of a display screen 1200 which is displayed on the display unit 1114. The operator initially operates the operation unit 1111 in the radiation imaging control apparatus 1110 to input patient information and inspection information for a subject, and then starts an inspection. The patient information includes the name of a patient, a patient identifier (ID), and the inspection information includes imaging information indicating details of image capturing to be performed on the subject. According to an inspection start operation, the radiation imaging control apparatus 1110 displays the display screen 1200 as illustrated in FIG. 10 on the display unit 1114.

The display screen 1200 which is displayed on the display unit 1114 displays a patient information display portion 1204 for representing the patient information input before starting the inspection, an imaging information display region 1205, and an image capturing method button 1206 for representing the inspection information. The image capturing method button 1206 includes, for example, an imaging portion and information about the radiation imaging control apparatus 1110 to be used. The control unit 1112 in the radiation imaging control apparatus 1110 transmits imaging conditions (including the tube voltage, tube current, and exposure time) set in response to the image capturing method button 1206 (image capturing method) to the radiation generation apparatus 1120, along with the input inspection information, and controls the radiation imaging apparatus 1115, thus preparing for radiation image capturing.

When the radiation imaging apparatus 1115 has prepared for radiation image capturing, the radiation imaging control apparatus 1110 enters the state ready for image capturing. When the radiation imaging control apparatus 1110 enters the state ready for image capturing, a message region 1203 displays a "Ready" message indicating the state ready for image capturing.

Subsequently, the operator checks the radiation image capturing method based on the display screen 1200 displayed on the display unit 1114 and then performs image capturing setting and subject positioning. After a series of operations of preparing for image capturing is completed, the operator confirms the state ready for image capturing with reference to the message region 1203, and then presses a radiation emission switch. In response to the radiation emission switch being pressed, the radiation imaging control apparatus 1110 causes the radiation generation apparatus 1120 to emit a radiation to the subject, and causes the radiation imaging apparatus 1115 to detect the radiation that has penetrated the subject. In this manner, radiation image capturing is performed. Along with radiation image capturing, the optical image acquisition apparatus 1130 also performs optical image capturing.

After radiation imaging capturing is completed, the control unit 1112 in the radiation imaging control apparatus 1110 acquires a radiation image from the radiation imaging apparatus 1115 and an optical image from the optical image acquisition apparatus 1130, and stores these images in the storage unit 1113. The radiation imaging control apparatus 1110 subjects the acquired radiation image to image processing based on a predetermined image processing condition. The predetermined image processing condition is predefined according to the image capturing method. After the image processing is completed, the radiation imaging control apparatus 1110 displays the radiation image having undergone the image processing in the radiation image display region 1201. The radiation image display region 1201 is a part of the display items displayed on the display unit 1114.

After a radiation image and an optical image are acquired, the image processing apparatus 1100 acquires the radiation image and the optical image from the storage unit 1113 via the image acquisition unit 1102. The abnormality detection unit 1103 then detects an abnormality in the acquired optical image. Here, the abnormality refers to a physical trauma, such as skin discoloration, swelling, and bleeding. When the abnormality detection unit 1103 detects an abnormality in the optical image, the display control unit 1104 causes the display unit 1114 to display an object based on abnormality information regarding the detected abnormality and the acquired radiation image. The operator can search for a foreign matter related to the abnormality in the radiation image based on the object based on the abnormality information. The display control unit 1104 in the image processing apparatus 1100 causes the display unit 1114 to display, for example, an object 1209 for abnormality notification display, at the position on the radiation image corresponding to the location on the optical image in which an abnormality is determined to be present. In a case where the operator wishes to change the contrast of the radiation image, the operator operates buttons, such as the contrast and luminance buttons, provided in an image processing setting region 1207.

Similarly, in a case where the operator wishes to change the clipping region of the output image, the operator operates an adjustment button provided in the image operation region 1202. For example, in order to attach a character string serving as image diagnosis information, the operator operates an Annotation button 1202d and the like to display the character string as an Annotation 1210 on the image in a superimposed manner. If the orientation of the image is not suitable for diagnosis, the operator performs geometric transform by using a Rotate button 1202a and an Invert button 1202b. As described above, the operator can perform additional image editing operations on the image displayed in the radiation image display region 1201.

The operator repeats the above-described procedures to capture all of radiation images according to the image capturing method in the imaging information display region 1205. After all image capturing is completed, the operator presses an End Inspection button 1208. This completes a series of inspections. After a series of inspections is completed, the radiation imaging control apparatus 1110 attaches the inspection information and image capturing conditions as accompanying information to the captured image and then outputs the image, for example, to the PACS 1150. At the time of completion of the inspection, the optical image acquired from the optical image acquisition apparatus 1130 may be canceled, or output to the PACS 1150 and then stored in association with the radiation image.

Figure 11:
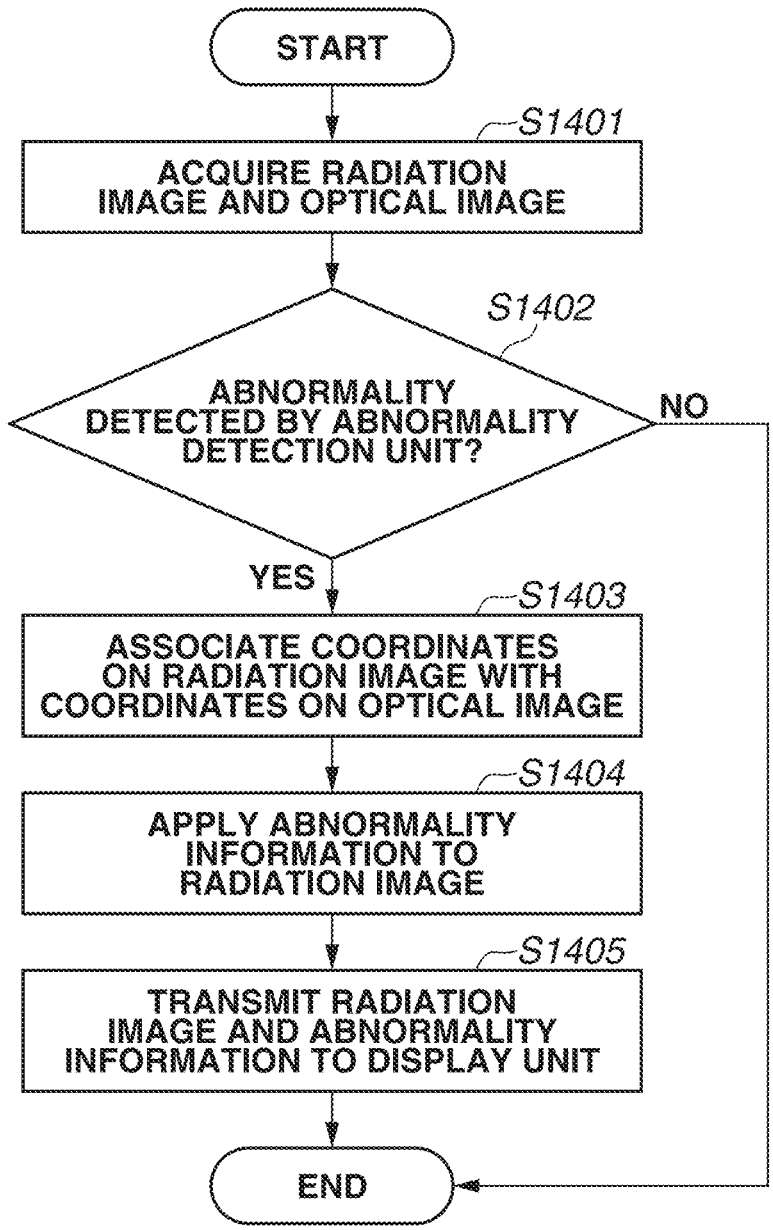
FIG. 11 is a flowchart illustrating processing of the image processing apparatus according to the third exemplary embodiment.

FIG. 11 is a flowchart illustrating the image processing apparatus 1100.

Initially, in step S1401, the image acquisition unit 1102 acquires a radiation image and an optical image from the storage unit 1113.

Next in step S1402, the abnormality detection unit 1103 subjects the optical image acquired by the image acquisition unit 1102 to abnormality detection processing. Examples of abnormalities include a physical trauma such as skin discoloration, swelling, bleeding, bruise, and fracture. For example, a CNN as one of techniques based on machine learning is used for abnormality detection.

The CNN is classified as supervised learning in machine learning. In the supervised learning, the learning of the CNN is performed by using training data including a pair of learning data and correct answer data supplied with the correct answer for the learning data. Thus, the CNN becomes available for an abnormality detection task. In this case, the training data includes correct answer data corresponding to respective abnormalities, and the CNN is trained.

When an optical image of the subject is input to the trained CNN, the CNN outputs the category of an abnormality and the coordinates of the abnormality. While a method by which the abnormality detection unit 1103 performs the detection processing through machine learning has been described above, the detection processing may be implemented through the conventional rule-based image processing technique.

In step S1403, the display control unit 1104 generates association information for associating the coordinates on the radiation image acquired by the image acquisition unit 1102 with the coordinates on the optical image. The association information is generated, for example, based on the irradiation field information. The irradiation field information refers to information indicating a range to be captured as a radiation image. In the acquired optical image, the region corresponding to the irradiation field region is brightly displayed by the light indicating the irradiation field in comparison with the other regions. Thus, trimming the irradiation field region in the optical image based on the brightness enables acquisition of the association information in which the coordinates on the optical image is in association with the coordinates on the radiation image. The association information generation method is not determined only by the irradiation field information but may be determined based on, for example, positional deviations of the optical image acquisition apparatus 1130 and the tube 1121 for radiation image capturing, and positional information for each apparatus. Enlargement, reduction, rotation, and/or angle correction processing may be performed according to both acquired images. Features may be extracted from the images based on the machine learning technique, and the association may be performed based on the extracted features. Any association information with which the coordinates on both images can be associated is applicable, and generation of the association information may be implemented by any of known techniques. When the coordinates have been associated, specific coordinates on one image can be converted into the corresponding coordinates on the other image based on the association information.

In step S1404, the display control unit 1104 attaches an object to the radiation image based on the abnormality information including the category and coordinates of the abnormality detected by the abnormality detection unit 1103 and the association information for the calculated coordinates between the images. Any format is applicable for the object to be attached to the radiation image as long as the object can be displayed on the display unit 1114 to enable the user to check the coordinates corresponding to the detected abnormality on the radiation image. More specifically, the display control unit 1104 displays on the radiation image an object based on the abnormality information detected from the optical image based on the association information. For example, on the radiation image, the region corresponding to the coordinates of the detected abnormality may be highlighted, and the abnormality information detected in the vicinity of the display region may be superimposed. After abnormality information is attached to the radiation image the, the display control unit 1104 transmits the radiation image and the abnormality information to the display unit 1114. More specifically, the display control unit 1104 displays the abnormality detected in the optical image on the coordinates in the radiation image corresponding to the coordinates on the optical image, based on the detected abnormality information and the association information, which is a characterizing feature of the display control unit 1104.

The display unit 1114 displays the information transmitted from the display control unit 1104 in the radiation image display region 1201. This enables the operator to detect a foreign matter while the burden on the operator is reduced, by searching for a foreign matter related to the abnormality detected by the abnormality detection unit 1103 based on the coordinates corresponding to the abnormality.

In the present exemplary embodiment, an abnormality is detected from the optical image and an object based on the abnormality information for the detected abnormality is displayed together with the radiation image, thus assisting the operator to find a foreign matter.

Fourth Exemplary Embodiment

In the third exemplary embodiment, a description has been provided of an example in which the abnormality detection unit 1103 detects an abnormality and the coordinates of the abnormality from the optical image, and the display control unit 1104 reflects abnormality information regarding the detected abnormality, in the radiation image. In a fourth exemplary embodiment, a description will be provided of an example in which the operator inputs the abnormality information for the optical image.

Descriptions of similar configurations, functions, and operations to those of the above-described exemplary embodiments will be omitted. Differences between the present exemplary embodiment and the above-described exemplary embodiments will be mainly described below.

Figure 12:
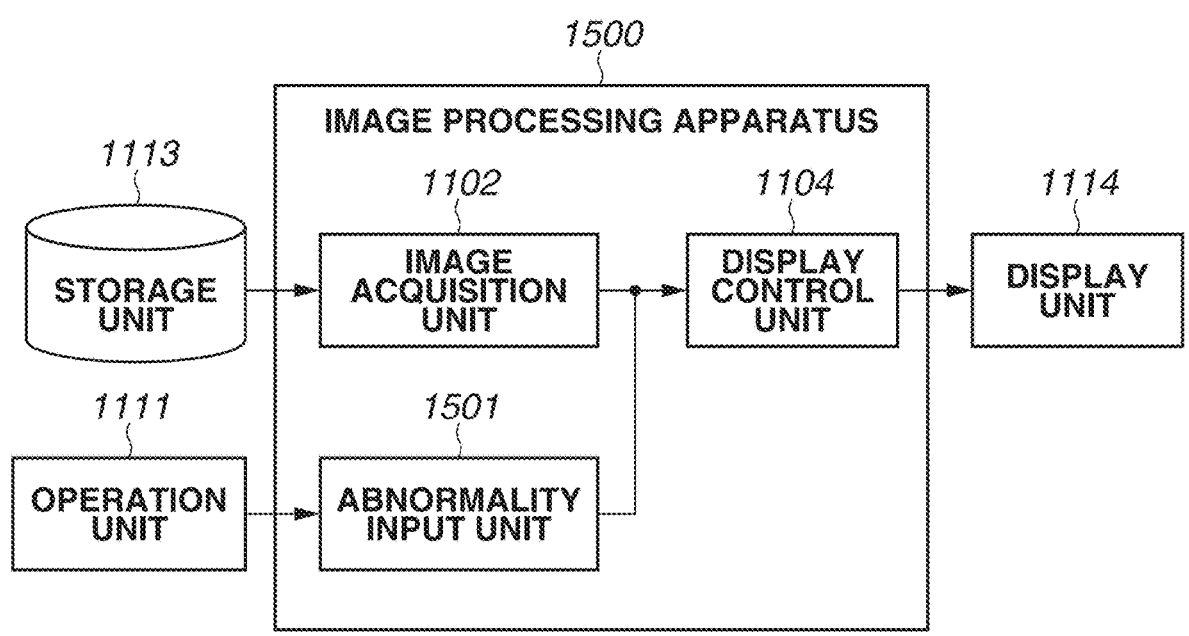
FIG. 12 illustrates a configuration of an image processing apparatus according to a fourth exemplary embodiment.

FIG. 12 illustrates an example of a configuration of an image processing apparatus 1500 in a radiation imaging system according to an exemplary embodiment of the present invention. According to the present exemplary embodiment, the operator operates the operation unit 1111 in the radiation imaging control apparatus 1110, and the image processing apparatus 1500 includes an abnormality input unit 1501 which receives an input of abnormality information from the operator. The operator operates the operation unit 1111 to input the location corresponding to an abnormality in the optical image to the abnormality input unit 1501 by using a mouse or the like.

Figure 13:
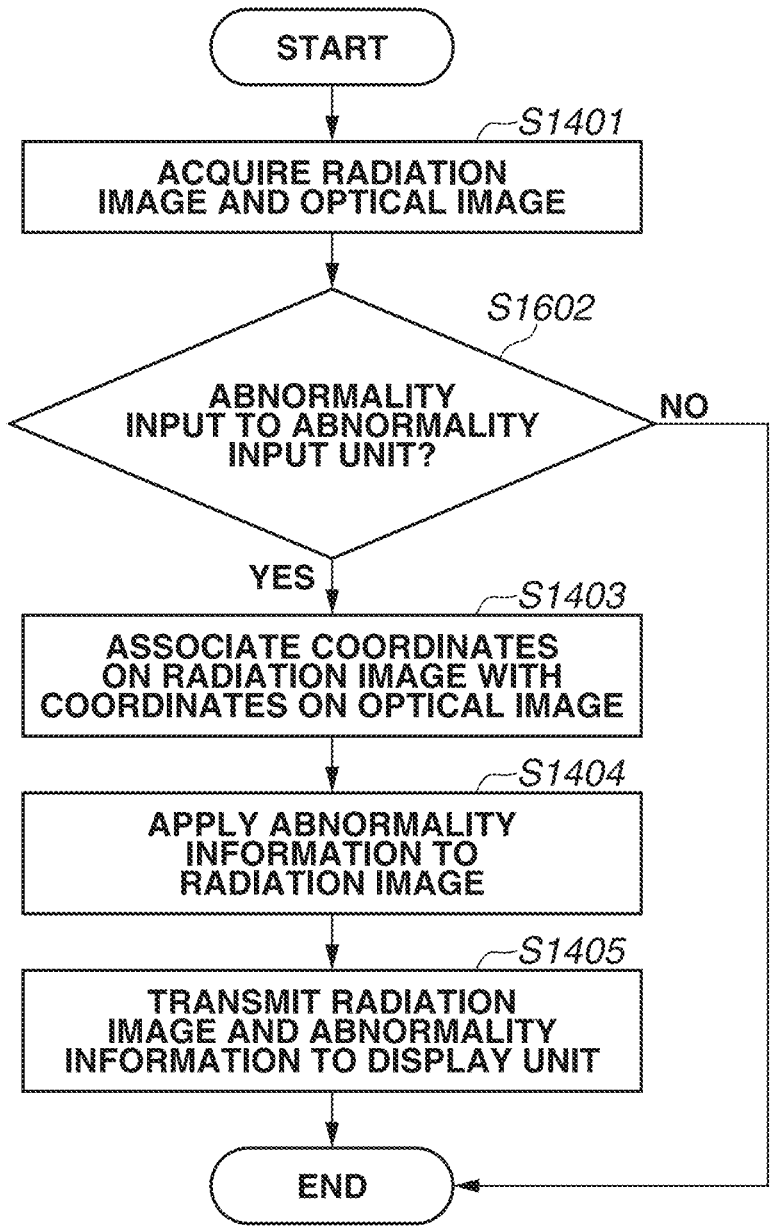
FIG. 13 is a flowchart illustrating processing of the image processing apparatus according to the fourth exemplary embodiment.

FIG. 13 is a flowchart illustrating processing of the image processing apparatus 1500 according to the present exemplary embodiment.

In step S1602, the operator inputs abnormality information for the optical image acquired by the image acquisition unit 1102. The abnormality information includes the category of an abnormality determined by the operator and the coordinates of the abnormality. The abnormality information input by the operator is processed in a manner similar to the third exemplary embodiment, and then displayed in the radiation image display region 1201 on the display unit 1114. The image processing apparatus 1500 may include the abnormality detection unit 1103 according to the third exemplary embodiment. The abnormality detection accuracy is improved by comparing the abnormality detected by the abnormality detection unit 1103 with the abnormality input to the abnormality input unit 1501 by the operator. In a case where the image processing apparatus 1100 includes the abnormality detection unit 1103 and the abnormality input unit 1501, for example, the abnormality detection unit 1103 may detect an abnormality in a region outside the region of the coordinates of the abnormality input by the abnormality input unit 1501. This configuration enables the abnormality detection unit 1103 to detect an abnormality based on the abnormality information input by the operator and a region where the abnormality information is not input by the operator. This prevents a foreign matter from being overlooked while reducing the burden on the operator.

Figure 14:
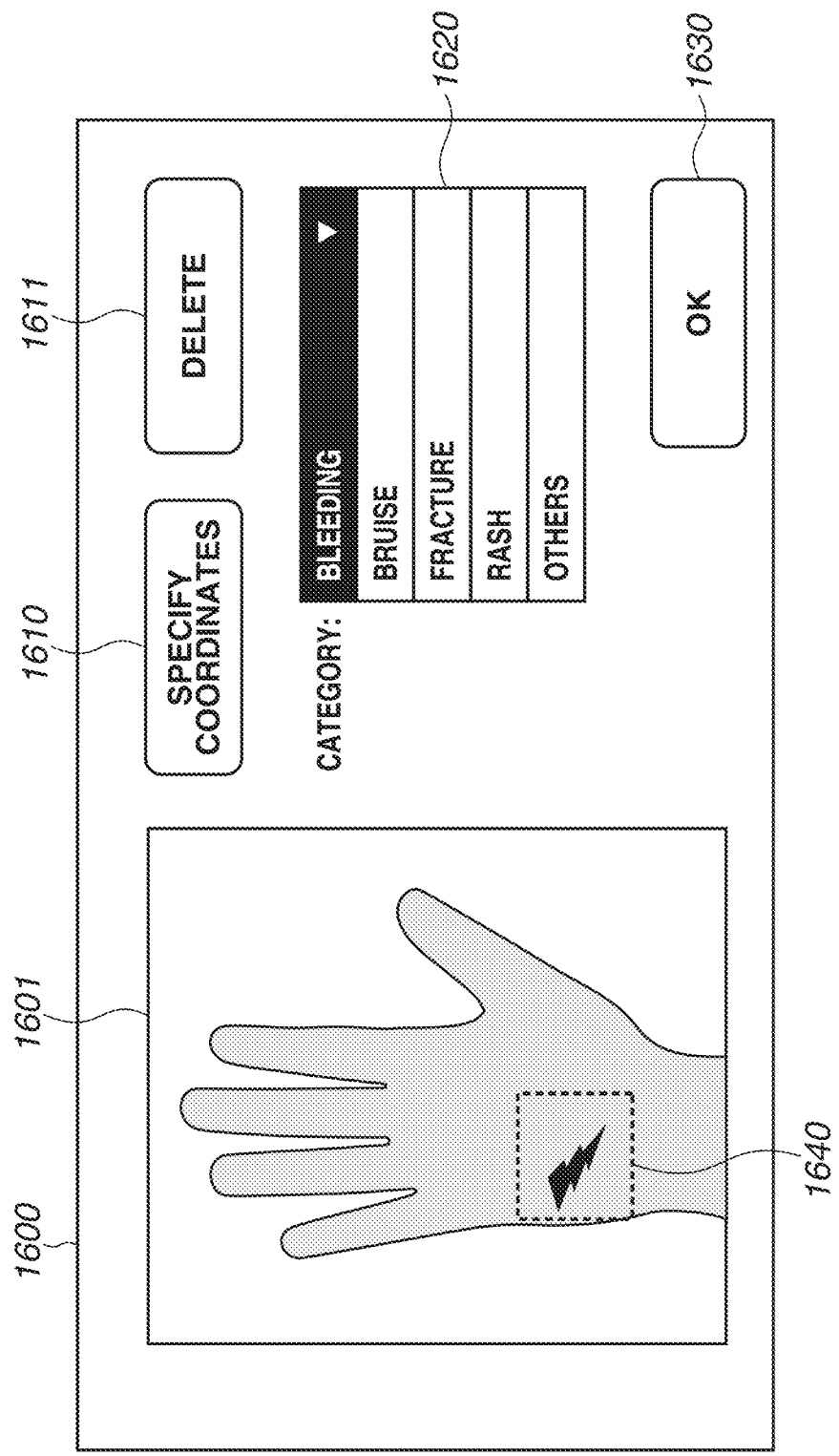
FIG. 14 illustrates an example of an abnormality input screen according to the fourth exemplary embodiment.

FIG. 14 illustrates an example of a graphical user interface (GUI) displayed on the display unit 1114 for the operator to input, for example, the abnormality information to the abnormality input unit 1501 via the operation unit 1111. After the radiation imaging control apparatus 1110 acquires an optical image from the optical image acquisition apparatus 1130, the radiation imaging control apparatus 1110 displays an abnormality input screen 1600 on the display unit 1114. The abnormality input screen 1600 may be implemented in such a manner that the abnormality input screen 1600 and the display screen 1200 are displayed on the same LCD in a switchable manner, or in such a manner that the abnormality input screen 1600 and the display screen 1200 are displayed at the same time on two different LCDs.

The acquired optical image is displayed in an optical image display portion 1601. In a case where the operator checks a displayed optical image and determines that there is an abnormality, the operator inputs abnormality information. The operator initially specifies the coordinates of the abnormality as an input of the abnormality information.

More specifically, the operator presses a Specify Coordinates (start coordinates specification) button 1610 to shift to the coordinates specification mode. Subsequently, the operator specifies the coordinates of the abnormality on the optical image display portion 1601 via the operation unit 1111, such as a mouse and a tablet. The coordinates corresponding to the specified abnormality is superimposed on the optical image display portion 1601 as an abnormality location specification region 1640. The position of the abnormality location specification region 1640 may be adjusted by a drag operation after the specification. If there is an error at the specified abnormality location, the input of the abnormality location may be deleted by the operator pressing a Delete (cancel abnormality location) button 1611 with the abnormality location specification region 1640 selected. After specifying the abnormality location specification region 1640 as the coordinates of the abnormality location, the operator inputs the category of the abnormality by using an abnormality category selection portion 1620 for abnormality category selection. The abnormality category selection portion 1620 is implemented by a drop box for selecting the category of an abnormality from a preset list, text boxes for inputting character strings by the operator, and the like. After inputting an abnormality location on the optical image, the operator presses an OK (complete abnormality location specification) button 1630. This completes the input of the abnormality location for the optical image and the abnormality input screen 1600 is hidden. In response to the abnormality information being input by the operator, the image processing apparatus 1500 performs coordinates conversion and information attachment via the display control unit 1104 based on the abnormality location input on the abnormality input screen 1600. The radiation image and the abnormality information to be displayed on the display unit 1114 are then generated.

According to the present exemplary embodiment, the operator inputs the abnormality information for the optical image, and the display control unit 1104 associates the coordinates on the radiation image with the coordinates on the optical image based on the abnormality information received by the image processing apparatus 1500 via the abnormality input unit 1501, and then transmits the information to the display unit 1114 in the radiation imaging control apparatus 1110. Accordingly, the display unit 1114 displays in the radiation image only an abnormality for which it is determined that check is to be performed on the radiation image by the operator but does not display the detected abnormality not affecting the inspection, thus reducing the burden on the operator.

Fifth Exemplary Embodiment

In the third and the fourth exemplary embodiments, an example has been described where the image processing apparatus controls the display of the abnormality information for a detected abnormality or input abnormality information, and instructs the display unit 1114 to display the information. In a fifth exemplary embodiment, a description will be provided of a configuration where the operator sets the category of a foreign matter to be displayed on the display unit 1114.

Descriptions of similar configurations, functions, and operations to those of the above-described exemplary embodiments will be omitted. Differences between the present exemplary embodiment and the above-described exemplary embodiment will be mainly described below.

FIG. 15 illustrates an example of a GUI for the operator to set the category of abnormality to be reflected in a radiation image of the display unit 1114. An abnormality category setting screen 1700 on the display unit 1114 includes a section for Category of Abnormality 1720 and check boxes 1710 for setting whether to reflect the abnormality information corresponding to respective abnormalities to the radiation image. Referring to the example in FIG. 15, bleeding and fracture are enabled as abnormalities to be reflected to the radiation image, and notifications on bruise and rash are disabled. By the operator pressing an OK button 1730, the operator's settings are stored in the storage unit 1113. The display control unit 1104 in the image processing apparatus 1100 issues a notification based on the set information.

Figure 16:
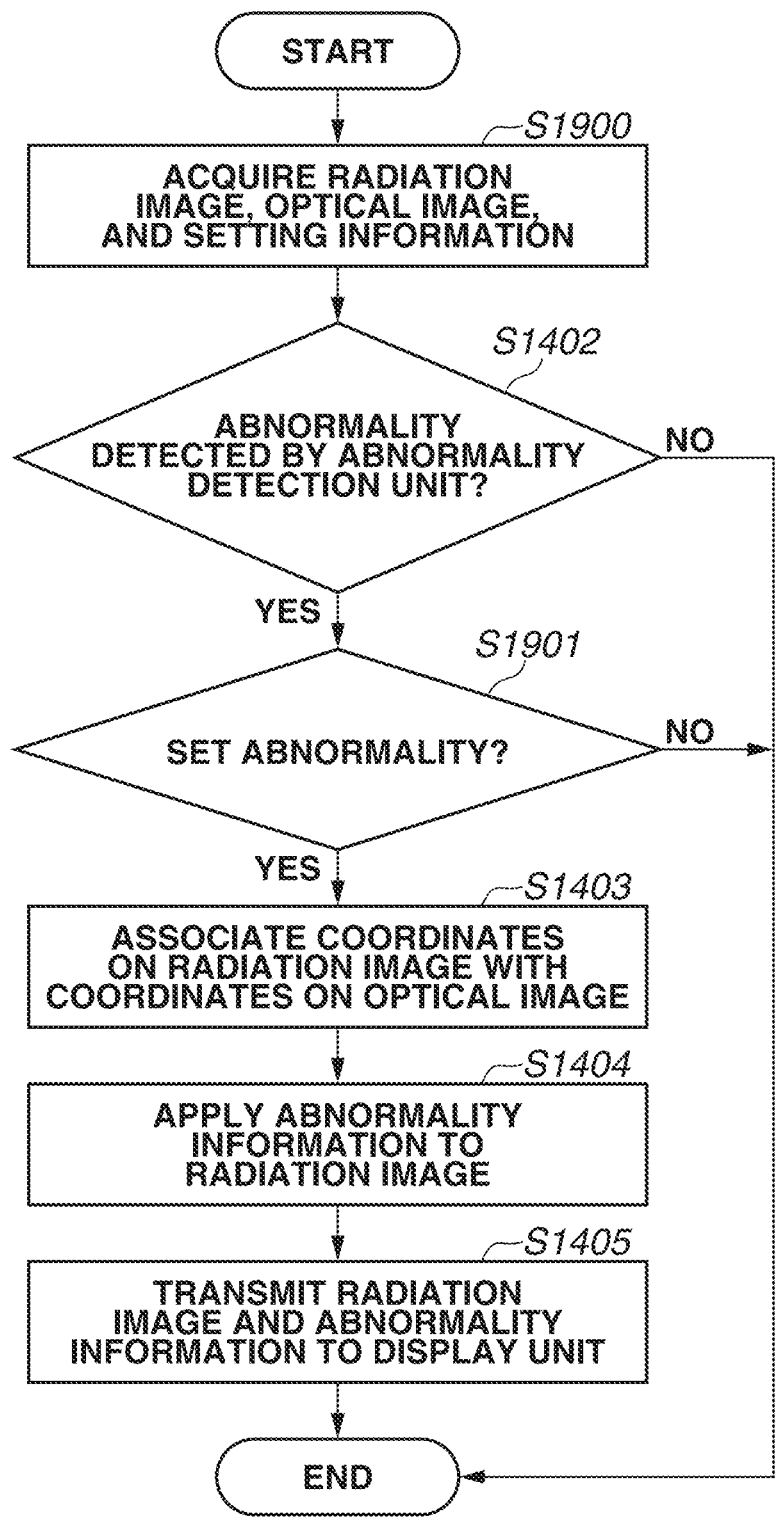
FIG. 16 is a flowchart illustrating processing of the image processing apparatus according to the fifth exemplary embodiment.

FIG. 16 is a data flowchart illustrating abnormality notification display processing of the image processing apparatus 1100 according to the fifth exemplary embodiment. In step S1900, the image acquisition unit 1102 acquires a radiation image, an optical image, and setting information for an abnormality to be reflected to the radiation image, from the storage unit 1113.

In step S1901, the abnormality detection unit 1103 determines whether the abnormality detected by the abnormality detection unit 1103 is an abnormality to be reflected to the radiation image, based on the setting information for the abnormality acquired by the image acquisition unit 1102. If the abnormality detected by the abnormality detection unit 1103 is a set abnormality (YES, in step S1901), the image processing apparatus 1100 performs processing in the subsequent stages for the abnormality. If the detected abnormality corresponds to none of the set abnormalities (NO, in step S1901), the image processing apparatus 1100 ends the processing. An example case where bleeding and fracture are enabled, and notifications on bruise and rash are disabled, as illustrated in FIG. 15, will be described below. In this case, the image processing apparatus 1100 determines whether the abnormalities detected by the abnormality detection unit 1103 include an abnormality corresponding to bleeding or fracture. If the detected abnormalities include bleeding or fracture, the display control unit 1104 generates a radiation image to be displayed on the display unit 1114 based on the abnormality information determined to coincide with the radiation image and the setting information. If the abnormalities detected by the abnormality detection unit 1103 include bruise or rash, the display control unit 1104 does not generate a radiation image to be displayed on the display unit 1114 for the abnormality. More specifically, the image processing apparatus 1100 acquires the setting information for the abnormality to be reflected to the radiation image set by the user, and displays an abnormality satisfying the setting information out of the abnormalities detected by the abnormality detection unit 1103, together with a radiation image, which is a characterizing feature of the image processing apparatus 1100.

According to the present exemplary embodiment, abnormality locations to be displayed on the radiation image display region 1201 are limited to abnormalities desired by the operator, and only necessary abnormalities are displayed on the radiation image. Thus, even if an abnormality not affecting the inspection is detected, the abnormality is not displayed, so that the burden on the operator is reduced.

Fourth Modification

Figure 17:
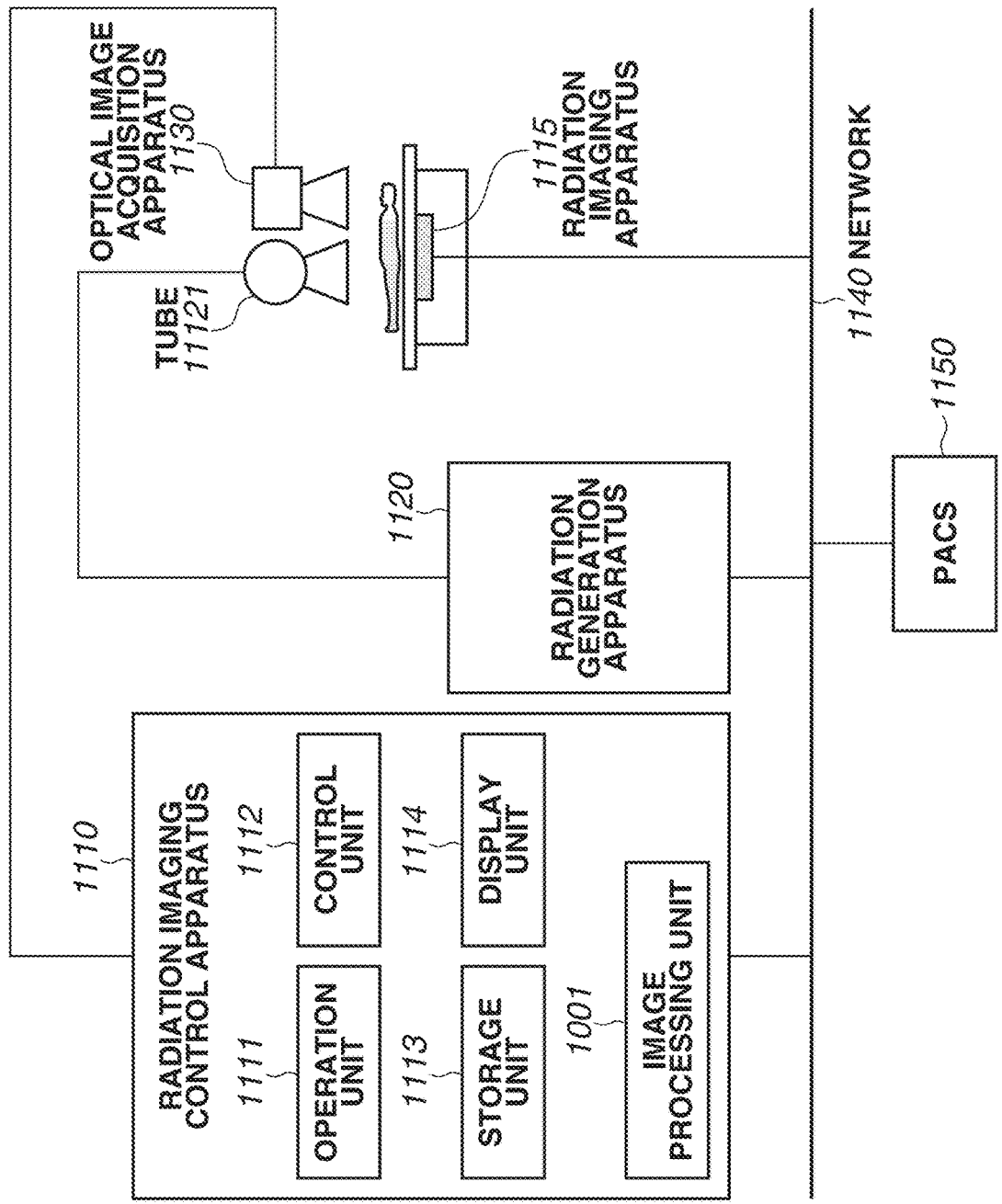
FIG. 17 illustrates a modification of a system configuration of the radiation imaging system.

The third to the fifth exemplary embodiments have been described above on the premise that the image processing apparatus 1100 which performs image processing is an independent apparatus. However, as illustrated in FIG. 17, the configuration of the image processing apparatus 1100 may be a part of the configuration in the radiation imaging control apparatus as an image processing unit 1001. The image processing apparatuses 1100 and the image processing unit 1001 may be a part of the configuration in other apparatuses or may be implemented on the cloud.

Other Embodiments

The present invention is also implemented by performing the following processing. More specifically, software (program) for implementing the functions of the above-described exemplary embodiments is supplied to a system or apparatus via a network or various types of storage media, and a computer (or CPU or micro processing unit (MPU)) of the system or apparatus reads and executes the program.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

The present invention is not limited to the above-described exemplary embodiments but can be modified and changed in diverse manners without departing from the spirit and scope thereof. Therefore, the following claims are appended to disclose the scope of the present invention.

The present invention enables preventing undesired radiation re-imaging by detecting a foreign matter which is likely to appear in a radiation image and displaying a warning before radiation image capturing.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiation imaging control apparatus comprising:
an image acquisition unit configured to acquire a captured image obtained by capturing an image of a subject by at least either one of an optical camera and an infrared camera;
a foreign matter detection unit configured to detect, in a case where a radiation image of the subject is to be acquired, a foreign matter which is likely to appear in the radiation image from the captured image acquired by the image acquisition unit;
a warning information generation unit configured to generate warning information regarding image capturing of a radiation image based on the foreign matter detection unit having detected a foreign matter in the captured image; and
a display control unit configured to issue a notification based on the warning information,
wherein the image acquisition unit acquires the captured image before the radiation image is acquired.

2. The radiation imaging control apparatus according to claim 1, wherein the image acquisition unit starts acquiring the captured image after preparation for capturing the radiation image is completed.

3. The radiation imaging control apparatus according to claim 1, wherein the foreign matter detection unit includes a foreign matter identification unit configured to identify a foreign matter from the captured image by using a machine learning algorithm.

4. The radiation imaging control apparatus according to claim 3, wherein the foreign matter identification unit outputs an identification result as a likelihood.

5. The radiation imaging control apparatus according to claim 4, wherein the foreign matter detection unit detects a foreign matter with a likelihood equal to or larger than a threshold value out of an output result by the foreign matter identification unit.

6. The radiation imaging control apparatus according to claim 1, wherein the warning information generation unit generates warning information indicating the foreign matter detected by the foreign matter detection unit and the position of the foreign matter.

7. The radiation imaging control apparatus according to claim 1, further comprising an irradiation field information generation unit configured to detect a position of an irradiation field provided by a radiation generation apparatus from the captured image and generate irradiation field information, wherein the foreign matter detection unit detects a foreign matter from an image region corresponding to the irradiation field information generated by the irradiation field information generation unit from the captured image acquired by the image acquisition unit.

8. The radiation imaging control apparatus according to claim 1, wherein, in a case where a plurality of foreign matters is detected by the foreign matter detection unit, the display control unit displays each of the plurality of detected foreign matters in an identifiable manner.

9. The radiation imaging control apparatus according to claim 8, wherein, in a case where a plurality of foreign matters is detected by the foreign matter detection unit, the display control unit displays each of the plurality of detected foreign matters in a switchable manner.

10. The radiation imaging control apparatus according to claim 1, wherein the display control unit displays an item for inputting whether a user has checked the foreign matter detected by the foreign matter detection unit.

11. A radiation imaging control method comprising:
acquiring a captured image obtained by capturing an image of a subject by at least either one of an optical camera and an infrared camera;
detecting, in a case where a radiation image of the subject is to be acquired, a foreign matter which is likely to appear in the radiation image from the acquired captured image;
generating warning information regarding image capturing of a radiation image based on a foreign matter having been detected in the captured image in the detecting; and
performing display control to issue a notification based on the warning information,
wherein the captured image is acquired before the radiation image is acquired.

12. A non-transitory computer-readable storage medium storing instructions that, when executed by a computer, cause the computer to perform the radiation imaging control method according to claim 11.

13. A radiation imaging system including an image acquisition apparatus including at least either one of an optical camera and an infrared camera that captures an image of a subject to acquire a captured image, a radiation imaging apparatus that performs radiation image capturing of the subject to acquire a radiation image, and a radiation imaging control apparatus that controls the radiation image capturing, wherein the radiation imaging control apparatus comprises:
a foreign matter detection unit configured to detect, in a case where a radiation image of the subject is to be acquired, detect a foreign matter which is likely to appear in the radiation image from the captured image acquired by the image acquisition apparatus;
a warning information generation unit configured to generate warning information regarding image capturing of a radiation image based on the foreign matter detection unit having detected a foreign matter in the captured image; and
a display control unit configured to issue a notification based on the warning information,
wherein the image acquisition apparatus acquires the captured image before the radiation imaging apparatus acquires the radiation image.

14. The radiation imaging system according to claim 13, wherein an image capturing range of the captured image acquired by the image acquisition apparatus has at least a region overlapping with an image capturing range of the radiation image acquired by the radiation imaging apparatus.

* * * * *